United States Patent
Hofmann et al.

(10) Patent No.: US 8,003,081 B2
(45) Date of Patent: *Aug. 23, 2011

(54) METHOD FOR IMPROVEMENT OF TOLERANCE FOR THERAPEUTICALLY EFFECTIVE AGENTS DELIVERED BY INHALATION

(75) Inventors: Thomas Hofmann, Doylestown, PA (US); Alan Bruce Montgomery, Medina, WA (US); Kevin Stapleton, Seattle, WA (US); William R. Baker, Bellevue, WA (US)

(73) Assignee: Gilead Sciences, Inc., Seattle, WA (US)

( * ) Notice: Subject to any disclaimer, the term of this patent is extended or adjusted under 35 U.S.C. 154(b) by 378 days.

This patent is subject to a terminal disclaimer.

(21) Appl. No.: 12/208,247

(22) Filed: Sep. 10, 2008

(65) Prior Publication Data

US 2009/0004279 A1    Jan. 1, 2009

Related U.S. Application Data

(62) Division of application No. 11/045,234, filed on Jan. 28, 2005, now Pat. No. 7,452,524.

(60) Provisional application No. 60/635,022, filed on Dec. 9, 2004, provisional application No. 60/539,836, filed on Jan. 27, 2004, provisional application No. 60/611,656, filed on Sep. 20, 2004.

(51) Int. Cl.
*A61K 9/00* (2006.01)
*A61K 9/12* (2006.01)
*A61K 9/14* (2006.01)

(52) U.S. Cl. ............... 424/45; 424/46; 424/43; 424/434

(58) Field of Classification Search ............... 424/45, 424/43, 434, 46
See application file for complete search history.

(56) References Cited

U.S. PATENT DOCUMENTS
2003/0171402 A1   9/2003   Gleich et al.
2003/0232019 A1 * 12/2003   Basu et al. .............. 424/46
2009/0041676 A1 *  2/2009   Hofmann et al. ......... 424/40

FOREIGN PATENT DOCUMENTS
WO      WO 98/37896 A1      9/1998

OTHER PUBLICATIONS

Loren W. Hunt, et al., Effect of Nebulized Lidocaine on Severe Glucocorticoid-Dependent Asthma, *Mayo Clin Proc*, 71:361-368 (1996).
Pari's eFlow(R), an Electronic Aerosol Device for Medication Delivery, Receives FDA 510(k) Market Clearance, *PARI Aerosol Research Institute*, pp. 1-2; May 18, 2004, Monterey, California USA.
Aldo T. Iacono, et al., Dose-Related Reversal of Acute Lung Rejection by Aerosolized Cyclosporine, *Am J Respir Crit Care Med*, V.155:1690-1698 (1997).
M. L. Decco, et al., Nebulized Lidocaine in the Treatment of Severe Asthma in Children: a Pilot Study, *Annals of Allergy, Asthma & Immunology*, V.82, No. 1, Jan. 1, 1999, Arlington Heights, IL, USA.
Supplementary European Search Report, Dec. 4, 2009, Munich, DE.
Abuan, Tammy B.S.N., Inhaled Lidocaine for the Treatment of Asthma: Lack of Efficacy in Two Double-Blind, Randomized, Placebo-Controlled Clinical Studies, Journal of Aerosol Medicine and Pulmonary Drug Delivery, vol. 23/6, pp. 381-388, 2010.
Poulton, Thomas J., M.D., et al., Cough suppression by Lidocaine, Anesthesiology, vol. 50/5, pp. 470-472, May 1979.
Sanders, Robert F., et al., Prolonged Suppression of Cough After Inhalation of Lidocaine in a Patient With Sarcoid, JAMA, vol. 252/17; pp. 2456-2457, Nov. 2, 1984.
Sherman, James M., Breaking the cycle: Lidocaine Therapy for Habit Cough, J. Florida M.A., vol. 84/5, pp. 308-309, Jun./Jul. 1997.
Trochtenberg, S., Nebulized lidocaine in the treatment of refractory cough, Chest, 105:1592-1593, 1994.
Udezue, Emanuel, MD, Lidocaine Inhalation for Cough Suppression, Clinical Notes, pp. 206-207, Oct. 6, 2000.

* cited by examiner

*Primary Examiner* — Mina Haghighatian
(74) *Attorney, Agent, or Firm* — Peters Verny, LLP

(57) ABSTRACT

A method for improvement of tolerance for therapeutically effective agents delivered by inhalation comprising a pretreatment of a patient with a nebulized lidocaine or a lidocaine-like compound administered immediately or up to about thirty minutes before administration of the primary therapeutically effective agent. The pretreatment of the patient with the nebulized lidocaine or a lidocaine-like compound improves airway tolerance and deposition of the agent in the lungs and makes such deposition more safe, efficacious, controllable and predictable. The method of the invention is especially useful for enhancement of deposition of immunosuppressive agents in the lung(s) of transplant patients, improved tolerance of the drugs by reducing cough, and improving pulmonary drug deposition.

21 Claims, 2 Drawing Sheets

METHOD FOR IMPROVEMENT OF TOLERANCE FOR THERAPEUTICALLY EFFECTIVE AGENTS DELIVERED BY INHALATION

This application is based on and claims priority of the Provisional applications Ser. No. 60/635,022, filed on Dec. 9, 2004, Ser. No. 60/539,836 filed on Jan. 27, 2004, 60/611,656 filed on Sep. 20, 2004 and on the PCT application PCT/US04/36926, filed on Nov. 4, 2004.

BACKGROUND OF THE INVENTION

1. Field of the Invention

The current invention concerns a method for improvement of tolerance for therapeutically effective agents delivered by inhalation said method comprising a pretreatment step utilizing a composition comprising a lidocaine or lidocaine-like compound, said composition delivered by nebulization using an electronic nebulizer. In particular, the invention concerns a method for improvement of tolerance for a primary therapeutically effective agent delivered by inhalation, said method comprising a pretreatment of a patient with a nebulized lidocaine or lidocaine-like compound administered immediately or up to about thirty minutes before administration of the primary therapeutically effective agent. The pretreatment of the patient with the nebulized lidocaine or lidocaine-like compounds improves airway tolerance and deposition of the therapeutically effective agent in the lungs and makes such deposition more safe, efficacious, controllable and predictable. The pretreatment step may also include oral or systemic administration of lidocaine or lidocaine-like compounds prior to administration of the primary therapeutic agent. The method of the invention is especially useful for enhancement of deposition of immunosuppressive agents in the lung(s) of lung transplant patients.

2. Background and Related Disclosures

A recent trend in medical drug delivery is directed toward targeted drug delivery to a region where the drug treatment is most efficacious, with a specific aim to avoid, if possible, the adverse reactions often observed with oral or other systemic drug delivery. Thus all diseases which affect lungs, currently treated with systemically administered drugs, would be preferentially treated with an aerosolized drug in an aerosol having specific parameters allowing a deposition of such drug in the lung region where the treatment is needed. However, aerosolized drug delivery may also be conveniently used for systemic administration of drugs, such as, for example, insulin, morphine, fentanyl and growth hormone, among others. The aerosolization of the drug and its administration through the lungs thus may substitute or complement the systemic drug delivery.

When the aerosolization is contemplated as a substitute drug delivery, the aerosol must be prepared in such a way that the aerosolized particles are predominantly deposited in the lung region where it is most efficacious and such deposition to other regions or to the upper respiratory airways, such as to the oropharyngeal area, is minimized.

In this regard, the lungs are divided into three regions. The upper lung covers the pharyngeal and tracheal region. The central lung covers lower trachea, bronchi and bronchiolar branches. The lower lung covers bronchioli and alveoli. Drugs administered via aerosol intended for delivery of the drugs to the lungs are administered in the aerosol directed to the central or lower lungs. Drugs administered via aerosol intended for systemic absorption are administered in the aerosol directed to the lower lungs, particularly to the deposition in alveoli from where the drug is absorbed into the general circulation. Additionally, the deposition in the mouth and nose, that is in the oropharyngeal area, must be avoided.

Depending on the region where the drug should be deposited, the prepared aerosol needs to have certain properties, particularly it needs to have a spectrum of particle sizes which reaches that particular region and which is preferably not deposited in other lung regions.

Aerosolized drug delivery provides certain advantages, such as safety and efficacy, compared to the systemic drug delivery. For example, since the drug is delivered directly to the target region, the amount of the drug needed to assert its therapeutic effect is lower than the systemic dose because the systemic dose must account for delivery of the drug throughout the whole body rather than only to the organ where the treatment is needed. Additionally, since the systemic delivery is avoided, there are none or lesser undesirable secondary effects. Finally, in cases where the aerosolized delivery substitutes oral delivery, there is a sparing effect for gastrointestinal tract, or circumvention of the intravenous route.

Despite all these advantages, up-to-date attempts to substitute the systemic treatments with aerosolized drug delivery has met with only partial success because some of the drugs, particularly more potent drugs such as for example, certain immunosuppressants, antibiotics and antifungals, are not well tolerated by lungs and such aerosolized delivery is thus limited.

Thus it would be desirable to have available a method and a means to improve delivery of and tolerance for these agents by inhalation.

A pretreatment with a nominal doses of the aerosolized lidocaine or lidocaine-like compounds prepared as a targeted aerosol and delivered by electronic nebulizer has been now found to improve such tolerance to the aerosolized drug delivery.

Lidocaine is a local and regional anesthetic currently approved for administration either as an injectable anesthetic for treatment of, for example, peripheral nerve, lumbar or caudal epidural block, as an intravenous infusion as an antiarrhythmic agent or in topical preparations for dermal, ocular and mucosal numbing (O'Neil M J. et al., Eds., *The Merck Index: A Encyclopedia of Chemicals Drugs and Biologicals*, 13th ed., Whitehouse Station, N.J.: Merck & Co., Inc. (2001).

Topical lidocaine has been previously also used prior to bronchoscopy to reduce airway reactivity and has been recommended as an aerosol for intractable cough and asthmatic tussive attacks (*Chest*, 105(5):1592-3 (1994), *JAMA*, 252(17):2456-7 (1984), *Anaesthesia*, 49(2):182 (1994) and *Chest*, 69(6):747-51 (1976)).

Adverse events related to lidocaine are not uncommon and cases of anaphylactic reactions and acute respiratory distress syndrome (ARDS) upon pulmonary application have been reported, for example, in *Chest*, 81(5):644-5 (1982), *Chest*, 83(3):585 (1983) and *Chest*, 83(6):933-4 (1983).

Adverse events associated with aerosolized lidocaine include numbing of lips, tongue and oral mucosa, and impaired gag reflex (*Am. Rev. Respir. Dis.*, 122(6):823-8 (1980), *Eur. J. Anaesthesiol.*, 17(11):672-9 (2000) and *JAMA*, 236(6):562 (1976) have been described.

The chronic topical application of aerosolized lidocaine to the airways used in previous studies was not associated with systemic toxicity (*Mayo Clin. Proc.*, 71(4):361-8 (1996) and *Ann. Allergy Asthma Immunol.*, 82(1):29-32 (1991).

The efficacy of chronic nebulized lidocaine was evaluated in studies in groups of adult and pediatric subjects with severe asthma at the Mayo Clinic in Rochester, Minn. These studies demonstrated a steroid-sparing effect and significant reduction in hospitalizations. No drug related serious adverse experiences were reported and the majority of subjects with steroid dependent asthma were at least partially weaned from oral corticosteroids (*Int. J. Tuberc. Lung Dis.*, 1:5, Suppl 1:S 32 (1997)).

In addition, lidocaine aerosol application to the airways attenuated the bronchoconstriction reflex provoked by inhalation challenge with histamine and methacholine, and challenges with hyperosmolar and hypoosmolar solutions, such as water. *Am. J. Respir. Crit. Care Med.*, 154 (4 Pt 1):885-8 (1996) and *Chest*, 72(4):429-38 (1977).

Nonetheless, the administration of aerosolized lidocaine is not without problems and complications. For example, upon aerosolization of 100 mg dose of lidocaine administered in 2.5 ml of a 40 mg/ml solution using the PARI LC PLUS™ nebulizer, oral numbing of lips, tongue and mucosa, along with an impaired gag reflex occurred for approximately 15 minutes following the inhalation of lidocaine (*Am. J. Respir. Crit. Care Med.*, 163(5):A83 (2001). To overcome these reactions, it has been recommended that treated subjects should not eat or drink for one hour after aerosol treatment. Under this regime, lesser adverse events related to impaired swallowing or reflux have been reported.

In recent years, use of lidocaine was proposed also for treatment and suppression of cough, particularly for instances where respiratory examination, i.e. bronchoscopy, were to ensue, as such examination could be affected by a patient's cough (U.S. Pat. No. 6,362,197B1, *JAOA*, 98 (No 3): 170-172 (1998), *Chest*, 105:1592-93 (1994), *JAMA*, 252 (No 17) 2456-2457 (1984), *J. Canadian Assoc. Radiol.*, 22: 199-200 (1971), *Am. J. Emerg. Med.*, 19:206-207 (2001), *Regional Anesthetics*, 18:312-314 (1993), *British J. Pharmacol.*, 138: 407-416 (2003), *J. Appl. Physiol.*, 74: 1419-1424 (1993).

All prior disclosures dealing with lidocaine inhalation have certain shortcomings in terms of safety and tolerability of inhaled lidocaine. Safety concerns associated with the administration of lidocaine are oropharyngeal numbing with loss of gag reflex, risk of aspiration of fluids and food, moderate to severe bronchospasm and taste problems. In addition, the previously described treatments use a large amount of lidocaine delivered slowly over long periods of time that are not efficient enough to provide increase in the tolerance and safety of the lungs for delivery of certain drugs by inhalation.

Attempts to use an aerosolized lidocaine prior to administration of aerosolized cyclosporine are described in *Am. J. Respir. Crit. Care Med.*, 151: 516-521 (1995), *Am. J. Resoir. Crit. Care Med.*, 153: 1451-1455 (1996), and *Am. J. Respir. Crit. Care Med.*, 155: 1690-1698 (1997). In all these publications, the described administration of cyclosporine is preceded by administration of 5 ml of 2%, that is 100 mg, of aerosolized lidocaine alone or in combination with the aerosolized albuterol using a conventional or Inspiron jet nebulizer. These pretreatments were given in order to minimize cough, pharyngeal soreness, and breathlessness. However, due to incorrectly designed cyclosporine aerosol and lidocaine treatment and due to use of the inefficient nebulizer, cough, pharyngeal soreness, and breathlessness were not sufficiently ameliorated and were repeatedly observed together with acute breathlessness following the aerosol cyclosporine administration. In addition, the type of nebulizers (conventional or jet nebulizers) will deliver only approximately 10% of the nominal dose to the lungs, and substantially more (>20-30%) to the oropharynx. As a consequence, the patients experience substantial numbing of mouth and throat, and regurgitation. In these studies, the efficacy of aerosolized cyclosporine, determined for example by FEV1 improvement, was clearly correlated with the amount of cyclosporine deposited in the lungs. The amount of the deposited cyclosporine has now been found to be directly dependent on the pretreatment with aerosolized lidocaine. In other words, aerosolized cyclosporine would not be effective without inhaled lidocaine pretreatment.

From a safety standpoint, it is extremely important for transplant patients to be protected from regurgitation and aspiration, as the lungs are denervated after the operation. For this reason, it is very important to provide a delivery of lidocaine to the lungs that does not impair the gag reflex or cause aspiration.

From the brief description of the problems encountered with an aerosolized drug delivery, it is clear that there is a continuous need for improvement of airway tolerance and airway deposition for therapeutically effective drugs delivered by aerosolization.

A method for such improvement of tolerance would preferably comprise a pretreatment step comprising inhalation of the aerosolized lidocaine or lidocaine-like compounds delivering a therapeutically effective amount of 10, 40 or 100 mg of lidocaine or lidocaine-like compounds in one ml of saline by aerosolization in particle sizes being substantially within either 2 and 5 or 3.5 and 10 microns directly to the lower lung or to the endobronchial space of airways, in a shortest possible time limited to at most 3 minutes with minimal oropharyngeal numbing and regurgitation.

It is, therefore, a primary object of this invention to provide a method for improved tolerance for delivery of the aerosolized primary therapeutically effective agent and for increased deposition of the aerosolized agent by providing a safe, physiologically acceptable and efficacious inhalable lidocaine or lidocaine-like compound for inhalation using a pure, preservative free lidocaine or lidocaine-like compound solution having pH between 5.5 and 7.5 which formulation contains a sufficient but not excessive concentration of lidocaine or lidocaine-like compound to improve the tolerance and drug deposition of the aerosolized therapeutically effective agent, that can be efficiently aerosolized by nebulization using an especially adapted and modified electronic nebulizer into an aerosol having an MMAD within a range from 0.1 to 2, 2 to 5 or 3.5 to 10 μm, with a substantially monodisperse particle distribution spectrum, or a dry powder formulation with similar aerosol properties administered with a dry powder inhaler, both well tolerated by patients.

All patents, patent applications and publications cited herein are hereby incorporated by reference.

SUMMARY

One aspect of the current invention is an inhalable nebulized lidocaine or lidocaine-like compound for targeted pretreatment of the lung with an aerosolized lidocaine or lidocaine-like compound administered either into conducting central airways or into lower lungs prior to the administration of an aerosolized therapeutically effective drug.

Another aspect of the current invention is an inhalable lidocaine or lidocaine-like compound solution or powder used as a pretreatment prior to the aerosolized drug delivery, said solution or powder nebulized using an electronic nebulizer or inhaler with a substantially monodisperse particle spectrum (GSD<1.7) into an aerosol with MMAD in the range of about 2 to about 5 for a lower lung delivery, between about 3.5 μm to about 10 μm for central and upper lung drug delivery or between 0.1 to 2 μm for systemic delivery of drug by aerosol wherein said nebulizer delivers about or more than 90% of lidocaine or lidocaine-like compound.

Yet another aspect of the current invention is a method for improved tolerance for aerosolized drug delivery into lungs, said method comprising one or multiple administration of 1 ml of a nebulized lidocaine or lidocaine-like compound solution comprising 10, 40 or 100 mg of lidocaine or lidocaine-like compound dissolved in 1 ml of saline having pH between 5.0 and 7.5 predominantly into either conducting and central airways or into the lower lung, said solution nebulized into an aerosol with MMAD substantially in a range of from about 3.5 μm to about 10 μm for the upper and central lung delivery, from about 2 μm to about 5 μm for the lower lung delivery or between 0.1 to 2 μm for systemic delivery of drug by aerosol, said aerosol delivered within 1 to 2.5 minutes immediately prior or within 30 minutes before the administration of the aerosolized drug.

Still yet another aspect of the current invention is a dry powder formulation of lidocaine or lidocaine-like compound whose particle size distribution has an MMAD between about 2 to about 5 μm or about 3.5 μm to about 10 μm, depending on the region where the powder is to be deposited and such powder has a substantially monodisperse particle spectrum for efficient deposition of lidocaine or lidocaine-like compounds into conducting and central airways.

Still another aspect of the current invention is a lidocaine or lidocaine-like compound formulation comprising either about 10, 40 or 100 mg of lidocaine or lidocaine-like compound in a normal or diluted saline solution or other aqueous solvent containing chloride, wherein said formulation has a pH between 5.5 and 7.0, unbuffered, osmolality between 150 and 550 mOsm/kg, ion concentration between 31 and 300 mM of chloride as a permeant anion, viscosity smaller than 1.5 cp, which formulation is delivered by nebulization in about 1 ml of solution wherein the resulting aerosol has a MMAD between 2 and 5 μm or 3.5 and 10 μm and a relatively monodisperse particle spectrum and wherein said formulation is nebulized using an electronic nebulizer equipped with a vibrating perforated membrane.

Still yet another aspect of the current invention is a dry powder formulation comprising either about 10 or 40 mg of lidocaine or lidocaine-like compound, wherein said formulation is milled, spray dried or precipitated into a fine powder with a MMAD between about 3.5 μm and 10 μm and a relatively monodisperse particle distribution used for inhalation of the dry powder administered in conjunction with delivery of the therapeutic drug by aerosolization.

Another aspect of this invention is a two-part reconstitution system comprising lidocaine or lidocaine-like compound in a dry or lyophilized powder form and a diluent stored separately until use wherein, optionally, the primary therapeutic drug may also be included in this two part reconstitution system.

Still yet another aspect of this invention is a method for improvement of tolerance and enhancement of deposition of immunosuppressive agents in lung transplant patients.

Another aspect of the current invention is a method for improved tolerance for delivery of the aerosolized immunosuppressive agent to lung transplant patients, said method comprising one or multiple administration of about 1 ml of a nebulized lidocaine or lidocaine-like compound solution comprising 10, 40 or 100 mg of lidocaine or lidocaine-like compound dissolved in 1 ml of saline having pH between 5.0 and 7.5 predominantly into either conducting and central airways or into the lower lung, said solution nebulized into an aerosol with MMAD substantially in a range of from about 3.5 μm to about 10 μm for the upper and central lung delivery and from about 2 μm to about 5 μm for the lower lung delivery, said aerosol delivered within 1 to 2.5 minutes immediately prior or within 30 minutes before the administration of the aerosolized drug or, in alternative, in combination with a primary immunosuppressive agent, said immunosupressive agent delivered to the transplanted lung in an aerosol with MMAD substantially in a range from about 2 to about 5 μm.

Another aspect of the current invention is a method for improved tolerance for delivery of the aerosolized immunosuppressive agent to heart, kidney, liver or another organ transplant patients, said method comprising one or multiple administration of about 1 ml of a nebulized lidocaine or lidocaine-like compound solution comprising 10, 40 or 100 mg of lidocaine or lidocaine-like compound dissolved in 1 ml of saline having pH between 5.0 and 7.5 predominantly into either conducting and central airways or into the lower lung, said solution nebulized into an aerosol with MMAD substantially in a range of from about 3.5 μm to about 10 μm for the upper and central lung delivery or from about 2 μm to about 5 μm for the lower lung delivery, said aerosol delivered within 1 to 2.5 minutes immediately prior or within 30 minutes before the administration of the aerosolized drug or, in alternative, in combination with a primary immunosuppressive agent delivered into the systemic circulation in an aerosol with a MMAD substantially in a range from about 0.1 to about 2 μm, for prevention of transplant rejection.

Still yet another aspect of the current invention is a method for improvement of tolerance for smoke, smog, air pollution, dust or allergens, said method comprising steps:

a) preparing an inhalable formulation comprising about 10 mg, 40 mg or 100 mg of lidocaine or a lidocaine-like compound;

b) selecting an electronic nebulizer or meter dose inhaler able to generate aerosol of particle sizes substantially between 3.5 and 10 μm;

c) nebulizing said lidocaine or a lidocaine-like compound formulation into an aerosol having a mass median aerodynamic diameter of particles substantially between about 4 μm and about 5 μm having a geometric standard deviation lower than 1.7;

d) administering said aerosolized formulation to a human subject exposed to or following exposure to smoke, smog, air pollution, dust or allergens, immediately before or immediately after the exposure.

DEFINITIONS

Figure 1:
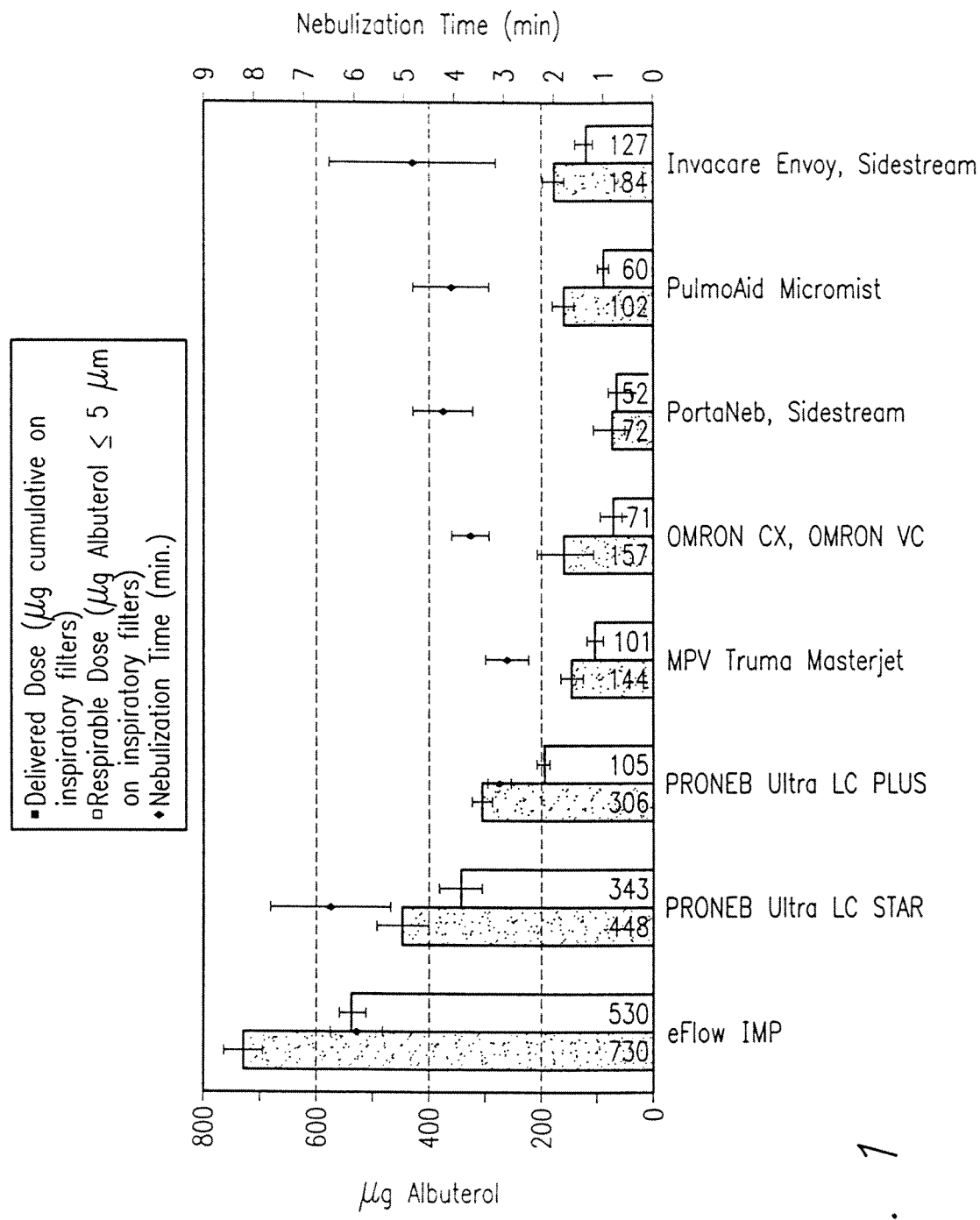
FIG. 1 shows results of comparative studies of eight different nebulizers determining a total delivered dose of the drug and respirable dose of albuterol in time.
Figure 2:
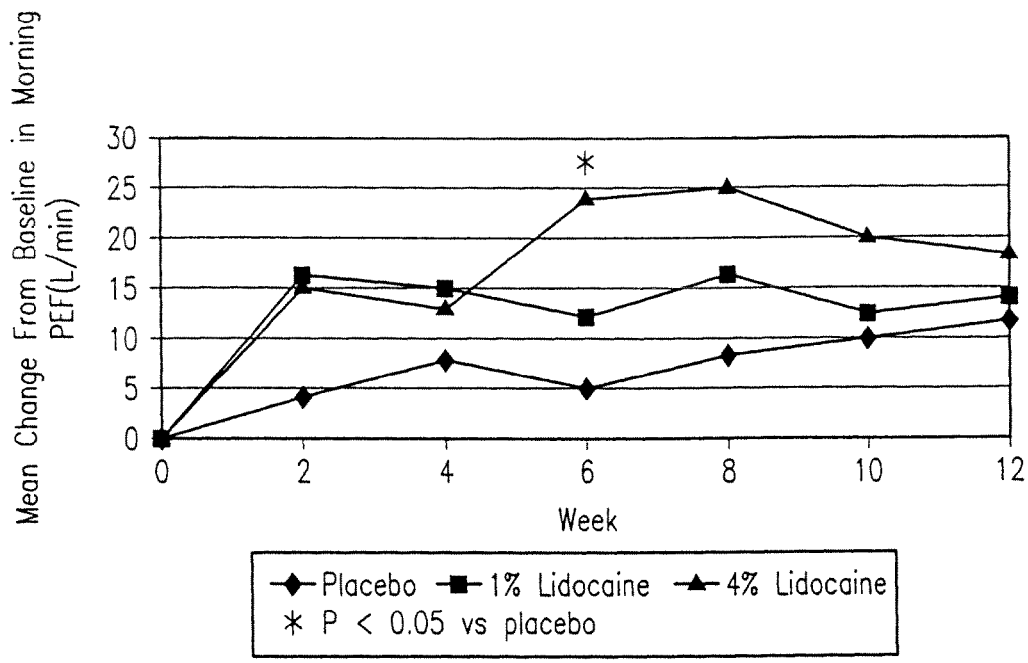
FIG. 2 is a graph showing a mean change baseline in morning peak expiratory flow following the administration of placebo, 1% lidocaine and 4% lidocaine inhalable solution.
Figure 3:
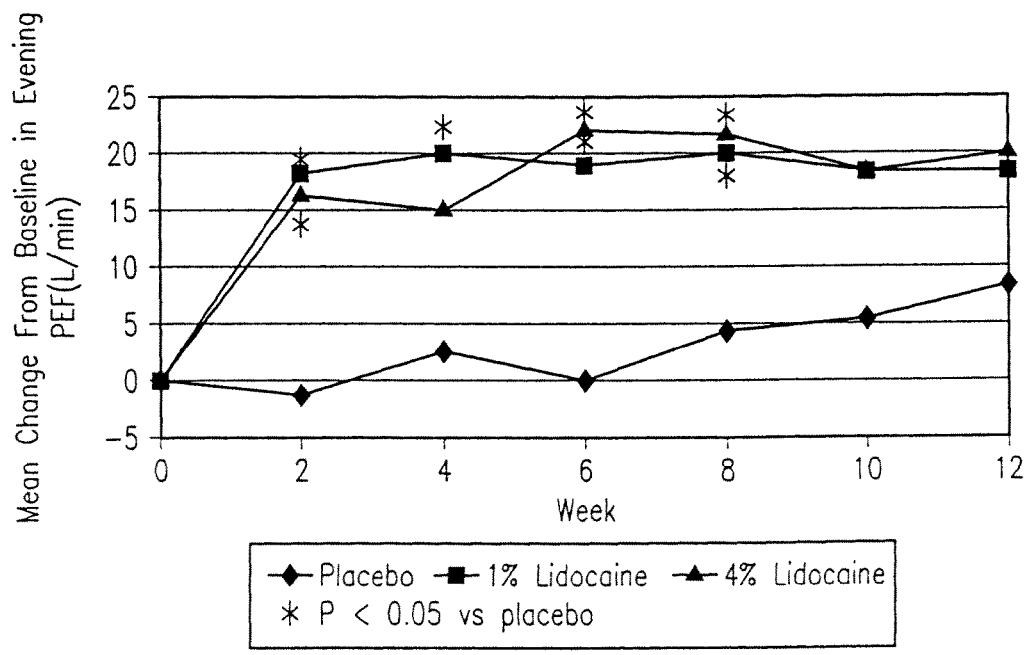
FIG. 3 is a graph showing a mean change baseline in evening peak expiratory flow following the administration of placebo, 1% lidocaine and 4% lidocaine inhalable solution.

As used herein:

"Drug", "pharmaceutical agent", "therapeutic agent" or "therapeutically effective agent" means a therapeutically active compound delivered into lungs or into a systemic circulation by inhalation.

"Primary drug", "primary agent", "primary pharmaceutical agent", "primary therapeutic agent" or "primary therapeutically effective agent" means any of the drugs covered by this invention that are administered by aerosolization of which the deposition and tolerance is improved or enhanced by a pretreatment with a solution of lidocaine or a lidocaine-like compound for inhalation administered either immediately prior to, within 30 minutes prior to the delivery of the primary drug or together with the delivery of the primary drug. The primary drug may be administered singly or in combination with another therapeutically effective drug or pharmaceutically acceptable excipient. The primary drug and lidocaine may be coadministered.

"MMAD" means mass median aerodynamic diameter.

"Normal saline" or "NS" means water solution containing 0.9% (w/v) NaCl.

"Diluted saline" means normal saline containing 0.9% (w/v) NaCl diluted into its lesser strength from about 0.04% to about 0.8%.

"Half normal saline" or "½ NS" means normal saline diluted to its half strength containing 0.45% (w/v) NaCl.

"Quarter normal saline" or "¼ NS" means normal saline diluted to its quarter strength containing 0.225% (w/v) NaCl.

"One tenth normal saline" or "¹⁄₁₀ NS" means normal saline diluted to its one tenth strength containing 0.09% (w/v) NaCl.

"One twentieth normal saline" or "¹⁄₂₀ NS" means normal saline diluted to its one tenth strength containing 0.045% (w/v) NaCl.

"Physiologically acceptable solution" means a saline diluted to between ¹⁄₁₀ NS and 1 NS or another aqueous solution comprising from about 31 to about 154 mM of chloride.

"Composition" means a lidocaine or lidocaine-like compound containing formulation which may additionally contain other components, such as excipients, diluents, isotonic solutions, buffers, etc.

"Formulation" means a specific composition formulated for specific use, such as for nebulization of a lidocaine or lidocaine-like compound containing solution or for nebulization of lidocaine or lidocaine-like compound dry powder.

"Lidocaine composition", "a lidocaine-like compound composition", "lidocaine formulation" or "a lidocaine-like compound formulation" means a composition or formulation comprising an indicated amount of lidocaine or a lidocaine-like compound.

"Central airways" means a section in respiratory tract defined by trachea, carina and bronchi.

"Carina" or "carina tracheae" means the ridge separating the opening the right and left main bronchi at their junction with the trachea.

"LSI" means lidocaine solution for inhalation.

"TOR" means total output rate.

"GSD" means geometric standard deviation.

"AE" means adverse event.

"SAE" means serious adverse event.

"AST" means aspartate aminotransferase.

"ALT" means alanine aminotransferase.

"ARDS" means acute respiratory distress syndrome.

"COPD" means chronic obstructive pulmonary disease.

"CS" means corticosteriod.

"ICS" means inhaled corticosteroid.

"OCS" means oral corticosteroids.

"FEF" means forced expiratory flow.

"FEV1" means forced expiratory volume in one second.

"FVC" means forced vital capacity.

"PEF" means peak expiratory flow.

"LFT" means liver function test.

"LLSI" means an inhalable solution comprising a lidocaine-like compound.

"MDI" means metered dose inhaler.

DETAILED DESCRIPTION OF THE INVENTION

The current invention concerns finding that an inhalable solution comprising lidocaine or a lidocaine-like compound administered prior to administration of an aerosolized primary therapeutically effective drug, or coadministered in combination with the primary drug at the same time, particularly of the primary drug that is not well tolerated, improves tolerance and enhances deposition of the aerosolized primary drug in the lungs.

The invention thus concerns a method for improvement of tolerance for aerosolized drug delivery wherein said aerosolized drug delivery is preceded by pretreatment with an aerosolized lidocaine or a lidocaine-like compound immediately before or up to about thirty minutes before administration of an aerosolized therapeutic drug or, in alternative, where such lidocaine or a lidocaine-like compound solution for inhalation is administered at the same time as the primary drug. Such pretreatment of the subject with the aerosolized lidocaine or a lidocaine-like compound improves airway tolerance and enhances deposition of the therapeutic agent in the lungs.

The method is particularly useful for improvement of tolerance and deposition of the primary drugs that are not well tolerated by the lungs and their use in the aerosolized form is thus limited. In this aspect, the invention is particularly useful for enhancing tolerance and deposition of immunosuppressant agents in lung, heart, kidney, liver or other organ transplant patients as well as enhancing the treatment of inflammatory pulmonary disease. Additionally, the method of the invention is suitable for reduction of airway susceptibility to environmental stimuli, such as smoke, pollutants and allergens wherein said lidocaine or a lidocaine-like compound formulation is administered to a person coming in contact with these environmental stimuli.

I. A Method for Improvement of Tolerance and Deposition for Aerosolized Drug Delivery A method for improvement of tolerance and deposition for an aerosolized primary drug comprises a pretreatment of the patient with a nominal amount of lidocaine or a lidocaine-like compound solution for inhalation.

Such pretreatment is administered either immediately prior to or within 30 minutes prior to the administration of these drugs by inhalation. Additionally, the lidocaine or a lidocaine-like compound solution for inhalation may be administered at the same time as the inhalable drug or even in combination with the inhalable primary drug or a combination of drugs.

Using the current method, the patients or transplant patients treated with a primary aerosolized drug selected from the exemplary drugs listed in Table 1, below, or with the drugs of the same type, are pretreated with a solution of lidocaine or a lidocaine-like compound for inhalation in order to overcome problems associated with low tolerance and deposition of these primary drugs during their delivery by aerosolization, or to overcome problems associated with transplant rejections, with treatment of pulmonary diseases and/or with increased sensitivity to environmental airway challenges from smoke, dust, allergens and air pollution.

The aim of this invention is to:

1) deliver an effective and safe dose of lidocaine or a lidocaine-like compound directly to conducting and central airways or to a site of action in the lungs as a pretreatment to delivery of the primary therapeutically effective agent through inhalation;

2) avoid significant systemic exposure to the primary therapeutic agent by providing conditions allowing reduction in the total dose of the primary therapeutic drug needed for treatment of the disease by administering said drug by inhalation; and 3) lower levels of the primary therapeutic agents delivered via inhalation by improving the tolerance of the lung to the aerosolized primary drug and its deposition thereby increasing its efficacy and enabling reduction in the total doses of the primary drugs needed for inhalation.

The invention thus in one aspect concerns lidocaine or lidocaine-like compounds formulated for use with a nebulizer or inhaler for targeted delivery of lidocaine or a lidocaine-like compound into conducting central airways or into the lower lungs, depending on the primary drug or on the area where the primary drug is to be deposited to be therapeutically effective. The method for improvement of tolerance for aerosolized drug at the same time reduces or eliminates the need for administration of these drugs orally or systemically. The aerosolized lidocaine or a lidocaine-like compound formulation delivered by an electronic nebulizer or by a dry powder or metered dose inhaler is administered in conjunction with administration of the inhalable primary drug and is typically administered either immediately before the administration of the aerosolized primary therapeutic agent or within thirty minutes before such administration. However, such inhalation treatment may be also administered in conjunction with the systemic administration of the primary drug, if needed.

The formulation comprising lidocaine or a lidocaine-like compound, administered in a daily dose from about 10, 40 or 100 mg per one ml of solvent, is delivered to the lungs in conjunction with the aerosolized pharmaceutical agent, typically once, twice or three times a day, or as many times as needed. Dosing depends on the dosing frequency of the primary therapeutic drug. Lidocaine or a lidocaine-like compound is formulated either as a solution or dry powder. Lidocaine or a lidocaine-like compound solution comprises 10, 40 or 100 mg of lidocaine hydrochloride or a lidocaine-like compound dissolved in one ml of normal or diluted saline having a pH between 5.5 and 7.5 per one dose delivery. The solution is nebulized into an aerosol having a mass median aerodynamic diameter (MMAD) within a range from about 2 to 5 µm, from about 3.5 and 10 µm, or preferably from about 3.5 and 5 µm, depending on the lung target region and is delivered in a substantially monodisperse particle spectrum using modified electronic nebulizers. Such a nebulizer is preferably equipped with a vibrating perforated membrane or is a metered dose inhaler.

Lidocaine or a lidocaine-like compound aerosolized according to the invention described herein is provided in a minimal effective dose and is deposited almost solely in the central airways or in the lower lung, bronchiole and alveoli, depending on the particle sizes of the aerosol, without any substantial residue of the anesthetic found in the oropharyngeal area or systemically.

The administration of the inhalable lidocaine or a lidocaine-like compound solution results in improvement of tolerance for the primary pharmaceutically effective agents and leads to more efficacious delivery of such agents. The lidocaine or a lidocaine-like compound solution nebulized using an electronic nebulizer preferably modified with a vibrating perforated membrane produces a substantially monodisperse particle spectrum resulting in a larger amount of lidocaine or a lidocaine-like compound deposited in the central airways, and in a reduced amount in the oropharynx.

The current invention thus provides an efficacious, safe, nonirritating, physiologically acceptable and compatible lidocaine or a lidocaine-like compound solution or dry powder for inhalation suitable for use in a method for improving tolerance for pharmaceutical agents delivered by aerosol. The method provides for fast delivery, within 1-2.5 minutes, at most 3 minutes, preferably 1-2 minutes, of efficacious amount of inhalable lidocaine or a lidocaine-like compound. For aerosolization, lidocaine or a lidocaine-like compound is delivered as a dry powder having particle size between 3.5 µm and 10 µm or as a solution comprising 10, 40 or 100 mg of lidocaine or a lidocaine-like compound dissolved in one ml of saline, having pH between 5.5 and 7.5 and osmolality between 200 and 550 mOsm/kg. The solution or dry powder are nebulized into an aerosol having a mass median aerodynamic diameter (MMAD) between 2 and 5 µm, 3.5 µm and 10 µm, using an electronic nebulizer, such as for example, PARI eFlow electronic nebulizer, 2 times daily, said nebulizer able to aerosolize the lidocaine or a lidocaine-like compound solution into particles of required sizes in a time period from about 1 to about 2.5 minutes.

Because of the high efficacy of the electronic nebulizer, only the minimal amount of lidocaine or a lidocaine-like compound is needed to achieve improvement of tolerance for aerosolized drug treatment, and the secondary undesirable symptoms such as bronchospasm, numbing of lips, tongue or pharyngeal region mucosa due to anesthetic properties of lidocaine, particularly upon extended time of exposure, or high systemic levels of lidocaine are eliminated or highly reduced.

The studies performed during development of this invention shows that LSI is well tolerated, safe and efficacious for pretreatment of primary drugs delivered by inhalation.

A. Target Areas of the Lungs

The target areas of the lungs where the primary drug needs to be deposited are upper, central conducting or lower airways. Depending on the lung disease which needs to be treated, the aerosolized primary drug is deposited at the area where the disease occurs and consequently will be delivered by aerosol having an appropriate MMAD. The lidocaine or a lidocaine-like compound solution for inhalation used as a pretreatment for improved tolerance and enhanced deposition of the primary drug is directed either to the central conducting airways, to the lower lungs or, in some instances, to the same area where the primary drug is directed.

The target areas for lidocaine or a lidocaine-like compound and the primary drug administration in the lungs differ depending on the disease and intended type of treatment. Thus, certain drugs are intended to be delivered into conducting and central airways comprised of trachea, carina and bronchi where infectious or inflammatory processes or bronchospasm occur. The other drugs are intended to be delivered primarily into the lower lungs where the pathogens which need to eradicated may reside, where the chemotherapeutic agent may need to be deposited or through where the drugs are administered into the systemic circulation. The inhalation therapy of these conditions thus targets the areas affected by specific diseases. However, in order to improve the tolerance to and deposition of the primary drug in the lungs, the lidocaine or a lidocaine-like compound for inhalation is formulated in such a way as to be predominantly delivered into the central conducting lung area largely responsible for lung intolerance to certain drugs, rather than where the primary therapeutic agent is to be deposited. However, it may also be formulated for delivery to the same area where the primary drug is deposited.

In the later instance, the lidocaine or a lidocaine-like compound solution for inhalation is aerosolized into particle sizes appropriate for the lung area where the therapeutic agent is to be deposited to be therapeutically most effective. Thus, for example, pentamidine used for eradication of *Pneumocystis carinii* needs to be deposited in the alveoli of the lower lungs. Consequently, the lidocaine or a lidocaine-like compound in a solution for inhalation is aerosolized for deposition into the central conducting airways or, similarly to the pentamidine solution, both are nebulized into an aerosol having predominantly particle sizes between 2 and 5 µm, to be delivered to the lower lungs. Similarly, primary drugs which are intended to enter the systemic circulation via alveoli parenchyma are formulated into aerosol having the range of particle sizes from about 0.1 to about 2 µm. On the other hand, antibiotics, steroids and such agents that are typically targeted to the upper or central lungs are nebulized into the aerosol having the particle sizes between 3.5 and 10 µm.

B. Primary Therapeutically Effective Agents

Almost any therapeutically effective agent, herein called a primary agent, used for treatment of lung or systemic diseases can be potentially delivered by inhalation. However, the primary targets for the method of this invention are therapeutically effective agents administered or to be administered by inhalation. Because of its anatomical and histological differences from other organs, some therapeutically effective agents may not be tolerated or well tolerated when administered by inhalation.

Table 1 below summarizes exemplary groups of therapeutic agents that can be delivered by inhalation, listing a type of the primary therapeutic agent, an exemplary therapeutic agent of that type, as well as the indication for its use.

TABLE 1

| Substance Type | Therapeutic Agent | Indication |
| --- | --- | --- |
| α-Antitrypsin | α-Proteinase-Inhibitor | α-deficiency |
| Antibiotic | Amikacin | Antibacterial, Bronchiectasis |
| Antibiotic | Carbenicillin | Antibacterial, Bronchiectasis |
| Antibiotic | Ceftazidim | Antibacterial |
| Antibiotic | Colistin | Antibacterial |
| Antibiotic | Gentamycin | Antibacterial, opthalmic |
| Antibiotic | Imipenem | Antibacterial |
| Antibiotic | Ticarcillin | Antibacterial |
| Antibiotic | Tobramycin | Antibacterial |
| Antibiotic | Vancomycin | Antibacterial |
| Antibiotic | Aztreonam | Antibacterial monobactam |
| Antibiotic | Fosfomycin | Antibacterial |
| Antibiotic | Rifampicin | Antibacterial |
| Antibiotic | Ciprofloxacin | Antibacterial |
| Antibiotic | Quinolones | Antibacterial |
| Antibiotic | Cefoperazone | Antibacterial |
| Antibiotic | Ciprofloxacin | Antibacterial |
| Antioxidant | Glutathion | Cystic Fibrosis |
| Antiprotozoan | Pentamidine | Pneumocystis carinii |
| Antifungal | Amphotericin B | HIV |
| Calcium | Nifedipin | High blood pressure |
| Calcium channel blocker | Verapamil | Pulmonary disease |
| Diuretic | Amiloride | Cystic Fibrosis |
| Diuretic | Benzamil | Cystic Fibrosis |
| Diuretic | Phenamil | Cystic Fibrosis |
| Diuretic | Furosemide | Cystic Fibrosis, Asthma |
| Diuretic | Piretanid | Asthma |
| Diuretic | Torasemid | Asthma |
| Protein | Heparine | Asthma |
| Immunosuppressant | Cyclosporine | Organ transplant rejection |
| Immunosuppressant | Prednisone | Organ transplant rejection |
| Immunosuppressant | Methotrexate | Organ transplant rejection |
| Immunosuppressant | Azathioprine | Organ transplant rejection |
| Immunosuppressant | Mycophenoline | Organ transplant rejection |
| Immunosuppressant | Mofetil | Organ transplant rejection |
| Immunosuppressant | Tacrolimus | Organ transplant rejection |

TABLE 1-continued

| Substance Type | Therapeutic Agent | Indication |
| --- | --- | --- |
| Immunosuppressant | Sirolimus | Organ transplant rejection |
| Cytokines | Gamma-Interferon | Tuberculosis, Cancer |
| Cytokines | Interleukin 2 | Cancer |
| Catecholamines | Adrenalin | Croup |
| Precursor | Retinoic Acid | Cancer |
| Corticosteroid | Beclomethasone | Inflammatory lung diseases |
| Analgesic | Fentanyl | Narcotic Analgesic, Pain |
| Antifungal | Fusafungin | Fungal diseases |
| Nucleotide | DNA | Gene therapy |
| Nucleotide | DNA analogs | Gene therapy |
| Salt | Magnesium Sulfate | Asthma |
| Mucolytics | Dextran | Cystic Fibrosis |
| Mucolytics | Dornase alfa | Cystic Fibrosis |
| Mucolytics | Hypertonic Saline (9% NaCl) | Cystic Fibrosis |
| Mucolytics | Mannitol | Cystic Fibrosis |
| Hepatic protector | N-Acetylcystein | Liver failure, Mucolytic |
| Cardiovascular | Nitroglycerine | Angina pectoris, congestive heart failure (CHF) |
| Cardiovascular | Nitroprusside-Na | Angina pectoris, (CHF) |
| Nucleotides | UTP, | Cystic Fibrosis |
| Opiates | Morphine | Pain, Drug dependence |
| Prostaglandins | Prostaglandin $I_2$ | Pulmonary hypertonus |
| Prostaglandins | Prostaglandin $E_1$ | Pulmonary hypertonus |
| Prostaglandins | Prostaglandin E | Pulmonary hypertonus |
| NSAID | Indomethacin | Arthritis |
| Steroid | Budesonide | Asthma, Chronic Obstructive Pulmonary Disease (COPD) |
| Steroid | Dexamethasone | Asthma, (COPD) |
| Surfactants | Poractant | Lung immaturity, Asthma |
| Surfactants | Calafactant | Lung immaturity, Asthma |
| Bronchodilator | Aminophylline | Asthma |
| Bronchodilator | Theophylline | Asthma |
| Antiviral | Ribavirin | Viral lung disease |
| Virustatika | Ribavirin | Viral lung disease |
| Growth factors | Granulocyte Macrophage Colony Stimulating Factor | Leucopenie |
| Hormone | Insulin | Diabetes |
| Hormone | Dehydroepiandrosterone | Asthma |
| Hormone | Prostacycline | Pulmonary Hypertension |
| Mucopolysacharide | Hyaluronic acid | Asthma, COPD |

Compounds listed in the Table 1 are illustrative only and it is to be understood that all other therapeutically effective agents of the same or different type suitable for treatment of the same or different indications are intended to be within a scope of this invention as long as they can be delivered by inhalation.

Certain compounds, such as colistin, tobramycin, pentamidine, cyclosporine, α-interferon, interleukin 2, amphotericin B and prostaglandins have been found to have particularly low deposition in lungs and often these drugs are not well tolerated or not tolerated at all by the lungs.

The pretreatment method using lidocaine or a lidocaine-like compounds in an aerosol is used prior to administration of any of these drugs singly or in combination.

II. Method for Improvement of Tolerance for and Deposition of Inhalable Therapeutic Agent in Lung Transplant Patients The method of this invention is also suitable for improvement of tolerance and enhancement of deposition of immunosupressive therapeutic agents, singly or in combination, in lung transplant patients.

Lung transplantation is often used for treatment of otherwise incurable pulmonary and cardiovascular diseases in patients with cystic fibrosis, idiopathic pulmonary fibrosis, pulmonary hypertension and bronchiectasis.

As in any other transplantation process, the key component of patient's survival is to assure that the lung transplant is not rejected by the patient's own immune system. Consequently, the immunosupressive therapy with immunosuppressive agents, such as cyclosporine, prednisone, methotrexate, azathioprine, mycophenoline, mofetil, sirolimus or tacrolimus is extremely important for lung transplant patient's survival.

Unfortunately, when administered systemically using either oral or intravenous routes, these agents assert such a potent immunosuppressive effect on the whole organism of the patient that all other immune responses needed to overcome viral, bacterial or parasitical opportunistic infections become also suppressed and the patient's life is seriously endangered.

Recently, in order to overcome these problems, treatment of the lung transplant recipients with aerosolized immunosuppressive drugs, particularly cyclosporine, was proposed and described in, for example, U.S. patent application Ser. No.: 09/244,792 filed on Feb. 5, 1999, Pub. No.: US 2002/0006901 A1, published on Jan. 17, 2002, hereby incorporated by reference in its entirety. Other references, discussed already in the Background and Related Disclosures section disclose the similar mode of treatment. All these disclosures describe administration of aerosolized cyclosporine for reversal of lung transplant rejection wherein the cyclosporine (300 mg) for aerosolization is dissolved in ethanol or propylene glycol (4.8 ml) and administered as an aerosol using either conventional or jet nebulizers in about 20-30 minutes inhalation times.

There are a few problems associated with the previously described aerosolized administration of cyclosporine.

First, because cyclosporine is not soluble in water, other solvents need to be used. Attempts to prepare aerosol from cyclosporine dissolved in ethanol or propylene glycol result in severe adverse reactions, such as cough, bronchospasm, acute breathlessness and pharyngeal soreness. Both ethanol and propylene glycol are known lung irritants and an extended time of delivery (20-30 minutes) described previously increases adverse reactions incidence. Ethanol is no longer used as a solvent for cyclosporine aerosolization. However, despite continuing reports that the patients' cough and other adverse reactions were so severe that the aerosolized cyclosporine treatment had to be often discontinued, propylene glycol is still currently used as a solvent for cyclosporine.

Second, the described cyclosporine aerosolization utilizes a relatively large amount of propylene glycol, approximately 4.8 ml for delivery of 300 mg of cyclosporine in an aerosol administered for about 20-30 minutes. Since the propylene glycol is a known irritant for eye and skin, it is currently not categorized as generally regarded as safe (GRAS). Short exposures to propylene glycol mist causes acute ocular and upper airway irritation in non-asthmatic patients *Handbook of Pharmaceutical Additives*, Eds. Ash Michael et al., P. 682 (2002); *Crit. Rev. Toxicol.*, 29:331-365 (1999) and *Occup. Environ. Med.*, 58:649-655 (2001). Such high volume of the solvent and a long exposure to it results in development of adverse reactions negatively affecting the patient.

It is well known and even admitted by inventors in '792 patent application that patients typically do not tolerate ethanol administered into the lung. Similarly, certain patients do not tolerate propylene glycol. The intolerance to aerosolized propylene glycol has been shown in humans (*Occup. Environ. Med.*, 58:649-655 (2001)).

Attempts to overcome these problems led to suggested pretreatment of the patients with 5 ml of 10% lidocaine solution administered by the conventional or jet nebulizer (*Am. J. Respir. Crit. Care Med.*, 151: 516-521 (1995), *Am. J. Respir. Crit. Care Med.*, 153: 1451-1455 (1996), and *Am. J. Respir. Crit. Care Med.*, 155: 1690-1698 (1997)). While some improvement had been achieved with this type of pretreatment, the above discussed adverse reactions together with oropharyngeal numbing and inhibition of the gag reflex were still observed following this procedure primarily because this pretreatment was ineffective due to use of the conventional or jet nebulizers. These nebulizers are known to deliver only about 5-10% of the total aerosolized dose and require much longer, 20-30 minutes, aerosolization time.

It has now been discovered that the tolerance for the immunosuppressive drugs and the degree of their deposition in lung transplant is improved by pretreatment of the lung transplant patient with lidocaine or a lidocaine-like compound solution or dry powder for inhalation, as described above, administered to the patient immediately prior to or within 30 minutes before the administration of the primary immunosuppressant drug in an aerosol delivered by an electronic nebulizer in about 1-2.5 minutes, at most in 3 minutes time, preferably 1-2 minutes, followed by administration of the primary immunosuppressive drug using the same type of the electronic nebulizer permitting a short period of delivery time of effective amount of the drug dissolved in a solvent.

Such pretreatment shortens patients exposure to the irritating solvent, permits more efficacious drug delivery of more than 90% of the aerosolized dose, results in higher drug deposition and improved tolerance of the lung transplant for treatment with the aerosolized immunosuppressant.

Approximate aerosolized doses are: cyclosporine (2.5-5 mg/kg/day), methotrexate (0.03 mg/kg/day), tacrolimus (0.03-0.05 mg/kg/day), sirolimus (0.05-0.2 mg/kg/day), prednisone (0.3 mg/kg/day), azathioprine (1-2 mg/kg/day) or another immunosuppressant. These doses assume that, depending on the delivery device for the primary immunosuppressant, approximately 10% or less of the nominal dose from the nebulizer will be deposited into the lungs.

Approximate oral or systemic doses are cyclosporine (50-200 mg/day), methotrexate (2-10 mg/day), tacrolimus (0.5-5 mg/day), sirolimus (2-5 mg/day), prednisone (5-50 mg/day) and azathioprine (50 mg/day).

III. Method for Improvement of Tolerance for Inhalable Therapeutic Agent in Organ Transplant Patients The method of this invention is additionally suitable for improvement of tolerance and enhancement of deposition of immunosuppressive therapeutic agents administered by aerosolization to organ transplant patients.

All organ transplants, such as heart, kidney, liver and other organ transplant are subject to the rejection by the patient's immune system. All transplant patients need to be treated with immunosuppressive agents. The problem, however, arises with a systemic administration of these agents as the immunosuppressive agents are typically very strong drugs that indiscriminately affect not only the transplant and prevent it from rejection but suppress the patient's immune system to a degree that although the transplant may not be rejected, all other immune reactions are suppressed and the patient is exposed to any opportunistic infection with which the patient may come in contact.

Consequently, the administration of the primary immunosuppressive drug by aerosolization provides an alternative route of administration which permits administration of smaller dosages of the primary drugs.

It has now been discovered that the tolerance for the immunosuppressive drugs and the degree of their deposition in a transplant recipient is improved by pretreatment of the lung transplant patient with a lidocaine or lidocaine-like compound solution or dry powder for inhalation administered to the patient immediately prior to or within 30 minutes before the administration of the primary immunosuppressant drug. The solution is administered in an aerosol delivered by the electronic nebulizer in about 1-2.5 minute, at most in 3 minutes time, wherein the efficacy of the drug delivery is more than 90% of the aerosolized dosage. The pretreatment step is followed by administration of the primary immunosuppressive drug using the same type of the electronic nebulizer permitting a short period of delivery time of effective amount (more than 90%) of the primary drug delivered in solvent. However, the primary immunosuppressive drugs may also be delivered by other nebulizers.

The pretreatment with lidocaine or lidocaine-like compound shortens patients exposure to the irritating solvent, permits more efficacious drug delivery, results in higher drug transfer through the parenchymal tissue of the lungs to the systemic circulation and improves tolerance of the lung for delivery of the aerosolized cyclosporine (2.5-5 mg/kg/day), methotrexate (0.03 mg/kg/day), tacrolimus (0.03-0.05 mg/kg/day), prednisone (0.3 mg/kg/day), azathioprine (1-2 mg/kg/day) or another immunosuppressant to the systemic circulation via lungs.

IV. Method for Improvement of Tolerance for Inhalable Therapeutic Agents for Treatment of Pulmonary Diseases The method of this invention is additionally also suitable for improvement of tolerance and enhancement of deposition of a primary therapeutically effective drug used for treatment of pulmonary diseases.

In this regard, the improvement of tolerance and enhancement of deposition of immunosupressive, antibacterial, antiviral or antiinflammatory therapeutic agents, or a combination thereof, delivered by nebulization to the lungs in patients suffering from a pulmonary disease is achieved by pretreatment of the patient with an inhalable solution comprising lidocaine or a lidocaine-like compound. Treatment of the pulmonary diseases, such as for example, bacterial or viral infections, parasitic diseases or inflammatory diseases such as asthma, cystic fibrosis, idiopathic pulmonary fibrosis, chronic bronchitis and allergic reactions, among others, with conventional primary drugs may be advantageously enhanced by using a pretreatment step of the current method wherein the patient is pretreated with a specifically formulated solution for inhalation comprising lidocaine or a lidocaine-like compound.

It has now been discovered that the tolerance for the conventional antibacterial, antiviral, antiinflammatory or immunosuppressive drugs may be improved and their deposition in the lungs enhanced by pretreatment of the patient with a lidocaine or lidocaine-like compound solution for inhalation administered to the patient immediately prior to or within 30 minutes before the administration of the primary drug in an aerosol delivered by the electronic nebulizer in about 1-2.5 minutes, at most in 3 minutes, followed by administration the primary drug. For the delivery of the primary drug the same type of the electronic nebulizer permitting a short period of delivery time of effective amount of the drug delivered in 1 ml of the solvent volume is preferably used. However, other types of nebulizers may also be used. Such pretreatment with lidocaine or a lidocaine-like compound shortens patients exposure to the irritating solvent and to lidocaine or lidocaine-like compound, and permits more efficacious drug delivery to the lungs or to the systemic circulation and improves tolerance of the lung for delivery of the aerosolized immunosuppressant, antiinflammatory, antiviral or antibacterial therapeutic agent to the lungs. The pretreatment of these diseases with lidocaine or lidocaine-like compounds may also enhance the antiinflammatory effect of the primary drug as there will likely be synergism between the lidocaine or a lidocaine-like compound and the primary drug.

In this regard, the U.S. patent application Ser. No. 09/244,792 filed on Feb. 5, 1999, Publ. No.: 2002/0006901, published on Jan. 17, 2002 is hereby incorporated by reference. All modes of treatment described therein may be conveniently improved and tolerance for and deposition of the drugs described therein enhanced by pretreatment with lidocaine or lidocaine-like compound according to this invention.

Additionally, and according to this invention, the above described method is also suitable for improvement of tolerance of an affected human subject exposed to smoke, smog, air pollution, dust or allergens, to these pollutants and for decreasing irritability in response to such exposure. The method for such improvement of tolerability comprises preparing an inhalable formulation comprising about 10 mg, 40 mg or 100 mg of lidocaine or a lidocaine-like compound, selecting an electronic nebulizer or meter dose inhaler able to generate aerosol of particle sizes substantially between 3.5 and 10 μm, nebulizing said lidocaine or a lidocaine-like compound formulation into an aerosol having a mass median aerodynamic diameter of particles substantially between about 4 μm and about 5 μm having a geometric standard deviation lower than 1.7 and administering said aerosolized formulation to a human subject exposed to or following exposure to smoke, smog, air pollution, dust or allergens, immediately before or immediately after the exposure.

V. Inhalable Compositions Comprising Lidocaine or Lidocaine-like Compounds

In one aspect, the current invention concerns a lidocaine formulation for inhalation suitable for efficacious delivery of lidocaine into the central conducting or lower airways by nebulization of the lidocaine solution (LSI) or a lidocaine dry powder, said lidocaine formulation used as a pretreatment for delivery of a primary drug by aerosolization.

In addition, compounds that are chemically and functionally similar to lidocaine, thereinafter lidocaine-like compounds, may be used in the same or similar manner according to the invention.

The invention is most preferably suitable for the delivery of lidocaine or lidocaine-like compounds by nebulization using electronic nebulizers, particularly a specifically modified PARI eFLOW™ electronic nebulizer. This nebulizer produces substantially monodisperse particles in predetermined particle sizes of about 0.1 to about 2 μm, about 2 to about 5 μm or about 3.5 to about 10 μm, the particle sizes being dependent upon an intended area of delivery. Lidocaine or lidocaine-like compounds prepared as a dry powder are nebulized using dry powder inhalers that produce aerosols with MMAD between about 3.5 μm and 10 μm, with a preferred MMAD being between 4 μm and 5 μm.

The aerosol of different particle sizes is necessary for efficacious delivery of lidocaine into the central conducting airways, to lower lung or through the alveoli parenchyma into the systemic circulation, while minimizing the oropharyngeal deposition of lidocaine anesthetic.

Selection of the nebulizer for practicing this invention is very important and an indivisible part of the invention because most previously used nebulizers for treatment of lung diseases are designed for administration of medications which need to be deposited in the peripheral airways. These nebulizers have low efficiency delivering only about 5-10% of the aerosolized dose and require much longer time for nebulization, typically 20-30 minutes.

Additionally, lidocaine for aerosolization needs to be formulated without preservatives and without epinephrine, in order to be tolerated by the lungs.

A. Lidocaine

Lidocaine is a local anesthetic known under the chemical name acetamide 2-(diethylamino)-N-(2,6-dimethylphenyl).

Lidocaine suitable for use in this invention is commercially available, for example from DSM Wyckoff, South Haven, Mich., and packaged by Cardinal Health Technologies-STW, Woodstock, Ill., as 1% (10 mg) or 4% (40 mg) lidocaine hydrochloride solution for intravenous use. Lidocaine solution for inhalation (LSI) is provided as a 1.0 mL sterile, preservative free, nonpyrogenic single dose ampule. The ampules contain either 10 or 40 mg of lidocaine hydrochloride, USP (1 mL 1% or 4% of lidocaine hydrochloride solution) having a pH range from 5.0 to 7.5. The sodium chloride content is 6.844 g/L of sodium chloride (USP) for 1% lidocaine, and 0.351 g/L of sodium chloride (USP) for 4% lidocaine. The osmolality for both solutions is approximately 275-300 mOsm/kg.

In this invention, lidocaine solution for inhalation (LSI) is intended to be used in combination with a specifically modified electronic nebulizer, preferably equipped with a vibrating perforated membrane, such as and preferably the PARI eFlow electronic nebulizer. Only in combination between LSI and an appropriate electronic nebulizer or inhaler will the advantages of this invention be valid and apparent. LSI is specifically formulated for inhalation, is preservative free and optimized regarding osmolarity, pH, and viscosity, to be adequate for nebulization via the electronic nebulizer.

B. Lidocaine-like Compounds

Lidocaine-like compounds are novel substituted acetanilides and benzamides described in the U.S. Provisional application Ser. No. 60/517,284, filed on Nov. 4, 2003 and in PCT application: PCT/US04/36926, filed on Nov. 4, 2004, by inventors, hereby incorporated by reference in its entirety.

Preparation, synthesis, formulations and delivery of substituted benzamides and acetanilides are disclosed in the provisional application 60/517,284.

Examples of lidocaine-like compounds of this invention include:

tetradecanoic acid [3-(2-diethylamino-acetylamino)-2,4-dimethyl-phenyl]-amide;
2-diethylamino-N-(2,6-dimethyl-3-tridecylamino-phenyl)-acetamide;
2-diethylamino-N-{2,6-dimethyl-3-[5-(4-phenyl-butoxy)-pentylamino]-phenyl}-acetamide;
N-(2-diethylamino-ethyl)-4-(4-trifluoromethoxy-benzylamino)-benzamide;
N-(2-diethylamino-ethyl)-4-(4-trifluoromethoxy-benzoylamido)-benzamide;
N-(2-diethylamino-ethyl)-4-(4-phenyl-benzoylamido)-benzamide;
2-[1,4']bipiperidinyl-1'-yl-N-[2,6-dimethyl-3-(4-phenyl-butylamino)-phenyl]-acetamide;
2-[1,4']bipiperidinyl-1'-yl-N-{2,6-dimethyl-3-[2-(4-trifluoromethoxy-phenyl)-ethylamino]-phenyl}-acetamide; and
2-[1,4']bipiperidinyl-1'-yl-N-(2,6-dimethyl-phenyl)-acetamide and the pharmaceutically acceptable salts of the foregoing compounds.

The lidocaine-like compounds, for the purposes of this invention, are delivered by inhalation as a pretreatment for the delivery of the primary drug by aerosolization and, similarly to lidocaine, these compounds improve tolerance of the lungs for the primary drug and enhance deposition of the drug at the lung area where the treatment is needed.

In all other aspects of the invention, that is the concentrations of the lidocaine-like compound, its formulation as dry powder or solution for inhalation, its delivery by aerosol, choice of the nebulizer, particle sizes and time of the delivery, the lidocaine-like compound is treated similarly to lidocaine and in all these aspects it may substitute for lidocaine.

C. Aerosolized Solution for Inhalation

Solution for nebulization comprising lidocaine or a lidocaine-like compound is formulated for most efficacious but safe delivery of aerosolized lidocaine or a lidocaine-like compound to the lung central or lower airways.

The lidocaine or a lidocaine-like compound composition comprises 10, 40 or 100 mg of lidocaine hydrochloride, lidocaine-like compound or a salt thereof delivered in a total volume of about 1 ml of saline for one inhalation dose. When formulated and administered according to the method of the invention, it delivers a therapeutically efficacious dose of lidocaine or a lidocaine-like compound to a target site in lungs in an amount of lidocaine or a lidocaine-like compound sufficient to improve tolerance and deposition for the inhalable primary therapeutic agent.

Combination of a composition of lidocaine or a lidocaine-like compound with an electronic nebulizer results in improved efficacy in inhalation. Such improved efficacy is expressed in terms of a substantially smaller amount of lidocaine or lidocaine-like compound and in terms of a substantially shorter delivery time needed to achieve in improvement of tolerance for a primary therapeutically effective drug. The electronic nebulizer, particularly the PARI eFlow nebulizer equipped with a vibrating perforated membrane obtained from PARI GmbH, Munich, Germany, produces an aerosol with a substantially monodisperse particle spectrum, permits delivery of a substantially whole dose (typically about or more than 90%) of lidocaine or a lidocaine-like compound into conducting, central airways or lower lungs without any substantial deposition of lidocaine or a lidocaine-like compound into oropharyngeal area or into the lower lungs. Such deposition is known to cause local numbing and loss of gag reflex in oropharyngeal area, and undesirable side effects and/or absorption or transport into the systemic circulation when delivered into the lower lungs. The PARI eFlow nebulizer is FDA (510-k) approved, and commercially available.

It is to be understood, however, that any device having the same ability to produce an aerosol having required aerosol characteristics available now or which will become available in the future is intended to be included within the scope of this invention. Examples of such devices are inhalers made by Omron, Boehringer Ingelheim, Chrysalis or Aerogen.

Each dose of lidocaine or a lidocaine-like compound solution contains a minimal yet efficacious amount of lidocaine or a lidocaine-like compound of either 10, 40 or 100 mg, per one ml dose, formulated and delivered in a smallest possible volume of about 1 ml of normal or diluted saline having osmolality between 275 and 300 mOsm/Kg and pH between about 5.0 and 7.5, preferably the pH of about 5.5-6. Lidocaine or a lidocaine-like compound solution for inhalation is adjusted to permit generation of an aerosol well tolerated by patients that minimizes the development of secondary undesirable side effects such as bronchospasm, numbing and has a minimal oropharyngeal deposition.

1. Safety

Primary requirement for the aerosolized local anesthetic formulation is its safety. Safety is measured by the anesthetic effect of the local anesthetic asserted on the other areas of the respiratory tract, by its deposition in other areas of the respiratory tract than those where the inhalable drug in intended to be deposited and by its numbing effect.

Bronchospasm of the lung is a one of the most observable symptoms, as described amply in the literature, and it is therefore important that the administration of aerosolized lidocaine or a lidocaine-like compound to the upper lungs does not cause bronchospasm because of any preservative contained in the inhalable formulation, or that bronchospasm is not caused by the particle sizes of the lidocaine or a lidocaine-like compound aerosols. With an uncontrolled delivery of lidocaine into the lungs, side effects such as systemic effects on the central nervous system, headache, tremor and dizziness are known to occur and are a measure of drug delivery safety. Even more importantly, a high oropharyngeal dose of lidocaine delivered with conventional or jet nebulizers, cause a high incidence of swallowing impairment, aspiration and regurgitation Since the lidocaine or a lidocaine-like compound for inhalation is formulated to contain only a nominal amount of lidocaine or a lidocaine-like compound and is delivered in particle sizes predominately deposited in targeted lung areas and not in oropharyngeal region, the method for improvement of tolerance and deposition of the primary inhalable drug by a pretreatment with lidocaine or a lidocaine-like compound according to the invention is both safe and efficacious.

2. Efficacy

Efficacy of the treatment is measured by the amount of the drug needed for the disease abatement, by the frequency of administration needed to suppress the disease symptoms, by the time necessary for delivery of the drug amount and by the percentage of the drug deposited in the specific target areas, as well as by a lack of deposition in the other areas. Very importantly, efficacy is measured by the patients' tolerance to environmental challenges to the airways, and his/her tolerance to smoke, dust, and air pollution.

Main advantages of the current formulations containing lidocaine or a lidocaine-like compound are its safety, its efficacy in improving the tolerance and deposition of the primary inhalable drug, its lesser anesthetic effect, its lesser oropharyngeal deposition, its lack of bronchospasm, its faster delivery, its targeted dosing, practicality and convenience of use as well as its long shelf-life, storage and ease of administration and manipulation of the nebulization device. Because of convenience, safety and practicality of the formulation and the nebulizer, the pretreatment may be provided in hospital setting, in the doctors office or at home.

Both the safety and efficacy requirements for aerosolized lidocaine or a lidocaine-like compound have now been found to be met by the lidocaine or a lidocaine-like compound formulation described herein delivered in the described manner using an electronic nebulizer able to deliver more than 90% of the aerosolized lidocaine or lidocaine-like compound.

3. Tolerance

The key parameters for airway tolerance for the lidocaine or a lidocaine-like compound formulation for inhalation during aerosolization exposure which needs to be met are osmolality, pH, lidocaine or a lidocaine-like compound concentration, ion concentration, viscosity and the absence of preservatives. These parameters are listed in Table 2, below.

TABLE 2

| Tolerability Parameters of Inhalable Lidocaine | |
|---|---|
| Osmolality | >150-<550 mOsm/kg |
| Ion Concentration | >31-<300 mM permeant anion |
| pH | 5.5 to 7.0, unbuffered |
| Viscosity | <1.5 cp |
| Drug Concentrations | 1-4% lidocaine HCl |
| Surfactants | None |
| Preservatives | None |
| Nebulization Time | <1-2.5 minutes |

As seen in Table 2, the lidocaine solution of the invention has osmolality between 150 and 550 mOsm/kg, ion concentration between 31 and 300 mM of the permeant anion, pH between 5.5 and 7.0 and viscosity lower than 1.5 centipoise. The lidocaine or concentration is either 1, 4 or rarely 10% (10, 40 or 100 mg) per ml of saline. Other than saline, there are no other preservatives which could cause secondary side effects. Nebulization time for administration of one ml of the lidocaine solution is about <1-2.5 minutes with at most 3 minutes when delivered with an electronic nebulizer (PARI eFlow) on the output rate of the eFlow electronic nebulizer which has TOR higher or equal to 0.4 g/minute. When the output rate is about 0.5 g/minute, the delivery of 1 ml of the lidocaine formulation is shortened to less than 2 minutes. Tolerability parameters are similar or the same for lidocaine-like compounds.

From the above description is it clear that the lidocaine or a lidocaine-like compound formulation for inhalation, as described herein, combined with the electronic nebulizer having the above described characteristics delivers the efficacious (about or more than 90%) amount of lidocaine or a lidocaine-like compound into lungs of the patient withing less than two minutes and at most at 2.5-3 minutes. The exposure of the patient to lidocaine or a lidocaine-like compound is thus substantially shortened compared to all prior attempts with inhalable lidocaine and such pretreatment is, therefore, better tolerated.

4. Dosage of Lidocaine or a Lidocaine-like Compound

The effective pretreatment requires a treatment regimen which provides sufficient amount of lidocaine or a lidocaine-like compound to permit the primary drug delivered by inhalation to be tolerated by the lungs and effective amount of said drug to be deposited in the target area.

A total daily dose of lidocaine or a lidocaine-like compound is therefore set to be between either about 10 or about 160 mg per day administered in one or several doses of 10, 40 or 100 mg per one dose. The total maximum daily amount of lidocaine should typically not exceed about 200 mg.

Typically, the formulation and the electronic nebulizer are selected to provide at least about 70%, preferably higher than 90%, efficacy of lidocaine or a lidocaine-like compound delivery to the conducting or central airways or to the lower lungs.

Determination of the effective dosage of administered lidocaine or a lidocaine-like compound and the regimen used for pretreatment of each patient depends on the responsiveness of the individual patient to the inhalation of the primary drug treatment.

The ultimate decisive factor is the improved tolerance for and deposition of the primary inhalable drug in the area where the drug is to be deposited. Thus, the frequency of the administration is correlated with the frequency of the treatment with the primary drug.

5. Effect of pH on Aerosol Formulation

The pH of the nebulized formulation containing lidocaine or a lidocaine-like compound is an important feature for pretreatment step with lidocaine or a lidocaine-like compound. Consequently, the saline solution used for preparation of an aerosol containing lidocaine or a lidocaine-like compound has certain requirements. Such aerosol has to provide osmolality between 275 and 300 mOsm/kg and at the same to maintain the optimal pH range between about pH 5.5 and 7.0, preferably between pH 5.5 and 6.5.

The control of pH of the formulation is necessary for safe and efficacious delivery of the nebulized lidocaine or a lidocaine-like compound. When the lidocaine or a lidocaine-like compound aerosol for nebulization is either more acidic or basic, that is outside of the range of pH given above, it can cause bronchospasm in central airways and exacerbate the disease or decrease rather than improve tolerance and deposition od the inhalable drug. Aerosolizable lidocaine or a lidocaine-like compound formulation having a pH between 5.5 and 7.0 is well tolerated and safe.

Therefore, the optimal pH of the nebulized lidocaine or a lidocaine-like compound used for pretreatment of the lungs before delivery of the primary drug is above pH 5.5, below 7.0 and is preferably between 5.5 and 6.5.

6. Effect of Salinity on the Inhalable Formulation

Patients suffering from acute or chronic lung disease have increased sensitivity to various chemical agents and have high incidence of bronchospasm incidents. Since the current method is designed for improvement of the inhalation drug delivery, the salinity of the solutions for aerosolization is very important.

The airways of a patient suffering from pulmonary diseases are particularly sensitive to hypotonic, hypertonic, acidic or alkaline conditions as well as to the excess or absence of a permanent ion chloride. Any imbalance in these conditions or a presence of chloride above certain values leads to bronchospasm or inflammatory events and/or exacerbated conditions which greatly impair delivery of the primary drugs by inhalation.

The preferred solution for nebulization of lidocaine or a lidocaine-like compound which is safe and tolerated by airways has a total osmolality between 275 and 300 mOsm/kg with a range of chloride concentration of between 31 mM and 300 mM. The given osmolality controls bronchospasm and the chloride concentration, as a permeant anion, contributes to a successful pretreatment according to the method of invention.

Normal saline (NS, 0.9%) contains 154 mM of chloride whereas 31 mM of chloride corresponds to about 0.2% normal saline. It has now been discovered that lidocaine or a lidocaine-like compound may be efficaciously delivered into central airways when dissolved in lesser than normal saline. The 1/20 N saline permits and assures a delivery of lidocaine or a lidocaine-like compound into central airways.

Consequently, the formulation for lidocaine or a lidocaine-like compound aerosol of the invention comprises either about 10, 40 or 100 mg, preferably about 40 mg, of lidocaine or a lidocaine-like compound dissolved in 1 ml of a normal or a diluted saline to from about 1/20 normal saline (NS) to about and at most to 1 normal saline solution.

7. Osmolality

Nebulization effects the osmolality of the solution and during nebulization osmolality can increase 11% to 62%, as compared with the pre-nebulization value. The peak increase in osmolality is typically observed between 10 and 15 minutes of nebulization.

This rise in osmolality may be explained by the mechanisms of nebulization. In a jet nebulizer, the aerosol is produced by the fluid shearing in a high velocity stream of dry gas. After primary droplet generation, water evaporates from the surface of the aerosol droplets to humidify the air thereby increasing the osmolality in the droplet. Approximately 99% of the droplets then return to the reservoir causing a continuous increase in the concentration of the solute in the liquid remaining in the nebulizer and a continuous increase in the osmolality of the aerosol droplets. Because of this increase in osmolality with time, it is important to restrict the nebulization time to no more than 10 minutes, and preferably to less then 3 minutes.

When using the Pari e-Flow electronic nebulizer or one of the other similarly equipped electronic nebulizers, the time of nebulization is shortened to 1-2.5 minutes, the above described increase in osmolality is avoided.

8. Ion Concentration and Permeability

The absence of a permeant anion in ultrasonically nebulized solutions is a stimulus for development of asthma even under iso-osmolar conditions.

Chloride was found to be an ideal permeant ion, with its presence mitigating some of the adverse effects caused by the hypertonicity of nebulized solutions. A chloride concentration between 31-300 mM was found to be optimal. If the ion used is not chloride, the selected alternative should freely permeate the respiratory mucosa.

Examples of alternative salts that produce suitable permeant anion and can be thus used as a substitute of the sodium chloride are calcium chloride, choline chloride, lysine monohydrochloride, potassium chloride, sodium bromide and sodium iodide.

However, while it is possible to use these substitutes, for the purpose of this invention, the sodium chloride anion is most preferable.

9. Viscosity

The rate of nebulization and particle size distribution is directly proportional to the viscosity of the solution, as the rate of nebulization and particle size decrease as the viscosity increases.

Consequently, the viscosity of the lidocaine or a lidocaine-like compound solution for inhalation should be kept near 1.5 cp.

10. Additives

As already stated above, the lidocaine or a lidocaine-like compound solution for inhalation is preservative free and preferably no other additives are used.

Any use or intent to use additives will require careful consideration concerning its effects on the airway tolerability and toxicity of the solution.

11. Lidocaine Formulations—Parameters

Parameters for two specific lidocaine formulations are seen in Table 3.

TABLE 3

Parameters 1% and 4% Lidocaine Solution For Inhalation

|  | 1% Lidocaine HCl | 4% Lidocaine HCl |
| --- | --- | --- |
| [Cl−] mM | 153 | 153 |
| Osmolality mOsm/kg | 291 | 286 |
| pH | 6.4 | 6.2 |
| ppm (Na+) |  | 160 |
| surface tension dynes/cm = mN/m |  | 58.32 |
| viscosity cps | 1.39 | 1.33 |
| Density | 1.00315 | 1.00239 |
| % label claim | 99 | 100 |

Parameters for inhalable solutions containing the lidocaine-like compounds are similar or the same.

All formulations are designed to be well tolerated and able to be reliably and completely nebulized to aerosol particles within the respirable size range of 2 µm and 5 µm or 3.5 µm to 10 µm, preferably within 4 µm and 5 µm, deposited rapidly and predominantly in the central or conducting airways unless a delivery is desired to the lower lungs or to the general circulation in which case the respirable size range between 0.1 and 2 µm may be used.

The doses are designed to contain as much as, but not more than, the necessary amount of a most active form of lidocaine or a lidocaine-like compound to achieve pretreatment according to the invention.

Patients can be sensitive to pH, osmolality, and ionic content of a nebulized solution. Therefore these parameters are adjusted to be compatible with lidocaine or a lidocaine-like compound chemistry and still tolerable to patients.

The formulation of the invention is nebulized into an aerosol with characteristics optimizing a delivery of the drug into the central airways largely affecting the tolerance of the lung to the primary drug delivery and enhancement of the primary drug deposition.

The formulation for pretreatment according to the invention must have a smallest possible aerosolizable volume able to deliver an effective dose of lidocaine or a lidocaine-like compound in the shortest possible time. The formulation must additionally provide conditions which would not adversely affect the functionality of the central airways. Consequently, the formulation must contain enough of the drug formulated under the conditions which allow its efficacious delivery while avoiding numbing of the upper respiratory tract and deposition in lower areas of the lung not affected by asthma. The new formulations according to the invention meets all these requirements.

12. Preferred Aerosolizable Formulations

The lidocaine or a lidocaine-like compound aerosolizable formulations comprise lidocaine or a lidocaine-like compound in amount about 10, 40 or 100 mg in about 1 ml of saline, having pH adjusted to between 5.0 and 7.0, said formulation delivered by aerosolization using an electronic nebulizer able to produce an aerosol having a mass median aerodynamic diameter (MMAD) between about 2 and 5 or 3.5 and 10 µm.

The most preferred formulation of the current invention comprises about 40 mg dose of lidocaine or a lidocaine-like compound dissolved in about 1 ml of normal or diluted saline, having pH adjusted to between 5.5 and 6.5, delivered by nebulization in aerosol particles having the mass median aerodynamic diameter predominantly between 2 and 5 or 3.5 and 10 µm, preferably between 4 µm and 5 µm, wherein said formulation is nebulized using preferably the PARI eFlow electronic nebulizer preferably also equipped with a vibrating perforated membrane.

D. Lidocaine or a Lidocaine-like Compound Dry Powder

An alternative way to deliver inhalable lidocaine or a lidocaine-like compound is by way of a dry inhalable powder. A dry powder formulation has potency, on a mass basis, which allows such alternative delivery of lidocaine or a lidocaine-like compound in a dry powder form using dry powder inhaler.

The lidocaine or a lidocaine-like compound may be administered to the central or conducting airways or into the lower lungs in the dry powder formulation using dry powder or metered dose inhalers as an alternative to a solution for inhalation delivered by nebulizer.

The dry powder formulation comprises from either 10, 40 or 100 mg, preferably 40 mg of lidocaine or a lidocaine-like compound. For the dry powder formulation of the invention, lidocaine or a lidocaine-like compound is processed to a dry powder. The dry powder may be prepared by various technologies known in the art. Examples of powder processing technologies include, but are not limited to media milling, jet milling, spray drying or particle precipitation techniques.

In this aspect, the invention provides a sufficiently potent formulation of lidocaine or a lidocaine-like compound formulated as a dry powder for use in a dry powder inhaler or metered dose inhaler such that when the powder is emitted from the device, the resulting aerosol has an MMAD between about 3.5 µm and 10 µm, preferably about 4 µm to about 5 µm.

The dry powder formulation is therefore practical and especially convenient for ambulatory use because it does not require dilution of the drug or other handling, it has an extended shelf-life and storage stability and the dry powder inhalation delivery devices are portable and do not require compressor or other attachments needed for nebulizers.

All techniques suitable for preparation of dry inhalable powders and any and all improvements thereof as well as any dry powder or meter dose inhaler are intended to be within the scope of the invention as long as they are able to provide and deliver particle sizes described above.

E. Shelf-Life Storage and Packaging

A shelf-life and stability of the formulation are important considerations for drug delivery. If the drug is degraded before nebulization, the amount of the delivered drug is smaller and unknown. The exact amount of the drug is impossible to determine. When the smaller and undetermined amount of the drug is delivered to the lung, the efficacy of the treatment could be compromised. Moreover, degradation processes of stored lidocaine or a lidocaine-like compound may generate materials that are poorly tolerated by patients. Consequently, is it of importance to provide a stable formulation having a reasonably long shelf-life.

For storage, lidocaine or a lidocaine-like compound for aerosolization is preferably formulated in a lyophilized dosage form. The lyophilized form of lidocaine or a lidocaine-like compound may be used for both a dry powder formulation for reconstitution before inhalation therapy or for preparation of the inhalable solution by aseptical reconstitution of the solution, or as a frozen solution, a liposomal suspension, or as microscopic particles.

The dry form of lidocaine or a lidocaine-like compound has at least 2 years long shelf-life. The inhalable solution for aerosolization provided for reconstitution in two separate components, one containing a dry or lyophilized lidocaine or a lidocaine-like compound or a salt thereof and a second containing an appropriate diluent, such as saline, has a similarly long shelf-life. The two component packaging permits reconstitution immediately prior to administration. This type of packaging prevents problems which could arise with a long-term stability of lidocaine or a lidocaine-like compound in aqueous solvents.

For packaging, the liquid form of lidocaine or a lidocaine-like compound (1%, 4% or 10%) may, for example, be conveniently supplied in one ml "Blow-Fill-Seal" vials, made of polyethylene plastic material permitting storage at room temperature. These ampules provide convenient and safe single use container. Specifically, the containers are made of the Low Density Polyethylene (LDPE) plastic such as commercially available plastics Huntsman Rexene 6010 and Flexicon Flexi-2114, with this or a different plastics or different material used as a overwrap. The plastic material chosen for storage is selected from those materials that avoid absorption of lidocaine or a lidocaine-like compound to the plastic walls of the vial, which is a common happenstance with certain regular plastics. The one ml fill volume provides a safe and efficacious amount of the drug, along with patient-convenient use of the plastic vial. In the "Blow-Fill-Seal" vials, covered with the plastic or aluminum overwrap, lidocaine or lidocaine-like compounds, in 1%, 4% or 10% solution, are stable for at least 9-12 months, at room temperature, without loss of strength. At accelerated conditions (40° C. and 75% relative humidity), both formulations remained active for at least 6 months. Using plastic Blow-Fill-Seal vials avoids problems with using glass bottles, and needle and syringe handling.

VI. Administration of Lidocaine or Lidocaine-like Compounds by Inhalation

Lidocaine or lidocaine-like compounds may be administered either as a solution or as a dry powder formulation.

A. Two Modes of Inhalable Administration

In one mode, administration of inhalable lidocaine or a lidocaine-like compound according to the invention is achieved with solution for inhalation comprising lidocaine or a lidocaine-like compound administered by nebulization using the electronic nebulizer. The appropriate amount of lidocaine or lidocaine-like compound is formulated in about one to three ml of solvent and delivered as an aerosol in particle sizes having MMAD between about 2 and 5 μm or between 3.5 and 10 μm, preferably between 4 and 5 μm.

In another mode, the inhalable lidocaine or a lidocaine-like compound is prepared and delivered as a lidocaine or a lidocaine-like compound dry powder using a metered dose or dry powder inhaler in a dry powder aerosol having the particle sizes between about 3.5 and 10 μm, preferably between 4 and 5 μm. In alternative, the drug may be prepared and stored as a powder and dissolved in saline just before administration, as described above.

B. Frequency of Dosing

The frequency of dosing is dependent on and dictated by the treatment regimen for a primary therapeutic agent. A typical frequency is from one to four times a day administration of the inhalable lidocaine or a lidocaine-like compound as a pretreatment to the inhalation of the primary drug.

The daily dose can be as small as 10 mg delivered once or several times a day in conjunction with the delivery of the primary drug. The upper limit per day is about 200 mg of lidocaine or a lidocaine-like compound per day delivered with preferred daily upper limit of 160 mg. For dry powder inhalation, the dose for one administration is, typically, between about 5 and 20 mg per one dose and at maximum such dose can reach 200 mg per day.

Preferably, the dosing frequency coincides with the dosing frequency of the aerosolized primary therapeutic agent, and the lidocaine or a lidocaine-like compound may be administered singly before the administration of the primary agent or co-administered with the primary agent in one aerosol.

VII. Devices for Delivery of Aerosolized Lidocaine or Lidocaine-like Compounds

A primary requirement of this invention is to deliver lidocaine or a lidocaine-like compound fast and efficiently, in smallest possible volume and shortest possible time to the central and conducting airways or, if desired, to the lower lungs, as a pretreatment step, prior to delivery of the primary drug by inhalation.

Drug delivery to the lungs is a function of the particle size distribution of the inhaled aerosol, of the delivery system, that is of the selected nebulizer or inhaler, and of the drug content in the particles. The effects of these aspects are well documented in, for example, in "*The Mechanics of Inhaled Pharmaceutical Aerosols*" by W. H. Finlay, Academic Press, (2001).

The lidocaine or lidocaine-like compounds of the invention described above are formulated in a solution permitting delivery of a nominal amount of the drug with high efficiency, provided that the aerosol generated by the nebulization meets criteria required for such efficient delivery. The electronic nebulizer which aerosolizes the formulation of lidocaine or a lidocaine-like compound dissolved in about one ml of solvent into substantially uniform particle sizes in times shorter than 2.5 minutes is an indivisible part of this invention.

A. Nebulizers Generally

The selected nebulizer must be able to efficiently aerosolize the formulation which has salinity, osmotic strength, and pH adjusted according to the invention as to permit generation of aerosol that is effective as a pretreatment step, delivers substantially all nebulized lidocaine or a lidocaine-like compound to the lungs in a smallest possible volume, time of the delivery is short and the aerosol is well tolerated by patients.

The selected nebulizer thus must be able to handle the formulation having a smallest possible aerosolizable volume and still be able to deliver effective dose of lidocaine or a lidocaine-like compound to the site of the action. Additionally, the aerosolized formulation must not impair the functionality of the upper airways and particularly must not be deposited in substantial amounts in the oropharyngeal region.

The inability of certain nebulizers to nebulize therapeutic quantities of drugs into uniform predetermined particle size aerosols is well known. Many commercially available nebulizers are able to aerosolize large volumes of the solution while delivering only about 10% of the volume and the drug to the lung. These nebulizers are inefficient and not suitable for delivery of lidocaine or a lidocaine-like compound according to this invention.

Most commonly used nebulizers for delivery of pharmaceutical aerosols produce aerosols with particle size ranges between 1 μm and 100 μm as this size range has the best balance of inhalability and ability to transport drug. Within this range, smaller particles tend to deposit deeper in the lungs, and larger particles tend to deposit oropharyngeally in the mouth and throat. Conversely, small particles contain much less drug (mass increases as the cube of the diameter) meaning that the time to deliver an efficacious dose to the lungs is much longer with smaller particles.

Additionally, most pharmaceutical aerosols currently available are polydisperse. Polydisperse aerosols consist of many particle sizes and consequently, the aerosols that are more polydisperse tend to deposit the particles over a wider region of the respiratory tract with a lesser dose of the drug deposited to the targeted area.

Previously, certain types of nebulizers, such as jet and ultrasonic nebulizers, have been shown to be able to produce and deliver more selectively aerosols with MMDS of between 1 μm and 5 μm. These aerosols might be suitable for treatment of pulmonary bacterial infections, however, they are not sufficiently efficacious and selective in producing particles which deposit the drug predominantly and efficiently in the conducting and central airways or in the lower lungs. Additionally, these nebulizers typically need larger volumes than 5 ml to administer sufficient amount of drug to obtain a therapeutic effect. Typically, however, under clinical conditions, even the jet nebulizers are only about 10% efficient. The amount deposited and absorbed in the lungs is thus a fraction of the 10% in spite of the large amounts of the drug placed in the nebulizer and nebulized.

There are quite a few nebulizer types currently commercially available. None of them but the electronic nebulizers are suitable for practicing this invention. Moreover, even among the electronic nebulizers, only those with a specific parameters are suitable for practicing this invention. The electronic nebulizer best suitable for practicing the current invention must be able to deliver about at least 70% but preferably 90% or more of lidocaine or lidocaine-like compound dissolved in about 1-3 ml, preferably about 1 ml, of solvent in time period shorter than 2.5 minutes, preferably around 1-1.5 minutes. The most preferred electronic nebulizer is PARI eFlow nebulizer preferably the one modified with a vibrating perforated membrane.

B. Nebulizers—Comparative Efficacy

Several commercially available nebulizers were tested for their suitability in practicing this invention. Results of these studies are summarized in Tables 3 and 4.

Tables 3 and 4 show results of comparing efficacy of various types of nebulizers to deposit the drug in lungs in vivo.

TABLE 3

Comparative Efficacy of Nebulizers

| NEBULIZER | Time/ Min. | Delivered Dose (μg) | Respirable Dose (μg) | Efficacy % |
|---|---|---|---|---|
| PARI eFlow | 6 | 730 | 536 | 100% |
| Pro Neb Ultra LC Star | 6.5 | 445 | 343 | 61% |
| Pro Neb Ultra LC Plus | 3.5 | 306 | 195 | 42% |
| MPV Truma Masterjet | 3.3 | 144 | 101 | 20% |
| OMRONCX: OMRONVC | 3.9 | 157 | 71 | 21.5% |
| Porta Neb Sidestream | 4.5 | 71 | 53 | 9.7% |
| Pulmo Aid Micromist | 4.2 | 162 | 90 | 22% |
| Invacare Envoy Side Stream | 5 | 184 | 127 | 25% |

Table 3 shows a time in minutes it takes various nebulizers to deposit a respirable dose of the drug.

As seen from results in Table 3, only the eFlow nebulizer was able to deliver 100% of the respirable drug dose in 6 minutes. All other nebulizers delivered between 9.7 and 61% of the drug.

As seen in Table 4, the 6 minutes time was set for delivery of the same respirable dosages as seen in Table 3.

TABLE 4

Comparative Efficacy of Nebulizers

| NEBULIZER | Time/ Min. | | Delivered Dose | μg | Respirable Dose |
|---|---|---|---|---|---|
| PARI eFlow | 6 | 730 | 100% | 536 | 100% |
| Pro Neb Ultra LC Star | 6 | 411 | 56% | 317 | 59% |
| Pro Neb Ultra LC Plus | 6 | 524 | 72% | 334 | 62% |
| MPV Truma Masterjet | 6 | 262 | 35% | 184 | 34% |
| OMRONCX: OMRONVC | 6 | 242 | 33% | 109 | 20% |
| Porta Neb Sidestream | 6 | 192 | 26% | 71 | 13% |
| Pulmo Aid Micromist | 6 | 231 | 31.5% | 128 | 24% |
| Invacare Envoy Sidestream | 6 | 220 | 30% | 152.4 | 28% |

When the time of nebulization was set to be 6 minutes, as seen in Table 4, again only the eFlow nebulizer delivered 100% of the respirable dose. All other nebulizers delivered much lower dose of the drug with percentage of the drug delivery only between 13-62% during the same time.

When the same nebulizers were evaluated in in vivo deposition studies, a lung deposition of approximately 40% of the total dose was seen when the electronic nebulizer was used. This was a marked increase in delivery efficiency compared to approximately 12% of the lung deposition of the dose administered with the jet PARI LC PLUS nebulizer.

Additionally, the oropharyngeal deposition observed with the electronic nebulizer was only about 5%, which is substantially lower than the oropharyngeal deposition seen when the jet nebulizers were used. Such deposition was observed to be approximately 16% with the jet PARI LC PLUS nebulizer. Further, the eFlow nebulizer has an output of 8 to 10 μL/sec which enables delivery of 1 ml of the drug in about 1-1.5 minutes, that is 2-5 times faster than the jet PARI Pro Neb Ultra LC PLUS nebulizer, the best performing nebulizer from those compared in Table 4, other than PARI e Flow.

The main advantage of the electronic nebulizers, particularly the PARI eFlow nebulizer, over other nebulizers is the speed of delivery. The PARI eFlow nebulizer can produce aerosol much faster than other nebulizers, decreasing the treatment time to less than 2.5 minutes, typically to 1 to 2 minutes. Also, in comparison to other nebulizers, the eFlow nebulizer has much less drug residue (residual volume) left in the device after the treatment, additionally decreasing the cost of the therapy.

By combining all these aspects, the modified PARI eFlow nebulizer can deliver a dose of medication to the lungs in average 2-5 times faster than jet or other unmodified electronic nebulizers, while decreasing side effects due to aerosol not deposited at the site of disease.

The electronic nebulizers generally, and the PARI eFlow electronic nebulizer particularly, are therefore, most preferred nebulizers primarily on the basis of allowing the formation of lidocaine or a lidocaine-like compound aerosol having a mass medium average diameter (MMAD) between 3.5 and 10 μm with MMAD predominantly between 4 μm to 5 μm with a substantially mondodisperse particle spectrum.

C. Preferred Electronic Nebulizers

The preferred nebulizers for practicing this invention are electronic nebulizers. Particularly preferred is the electronic PARI eFlow nebulizer.

Preferable electronic nebulizers are those electronic nebulizers that can produce aerosols with MMADs between about 3.5 and 10 μm, preferably 4 μm and 5 μm, with a relatively monodisperse particle spectrum of geometric standard deviation (GSD) smaller than 1.7. Examples of possible suitable electronic nebulizers are Aerogen Aeroneb Pro, Aerogen AeroNeb Go, Batelle White Phaser and its derivatives, Boehringer Spiromat, and the PARI eFlow nebulizer. All these nebulizers could potentially be used in practicing this invention.

The most preferred is the PARI eFlow® nebulizer manufactured by PARI GmbH of Starnberg, Germany. The PARI eFlow® nebulizer utilizes a novel perforated membrane aerosol generator which allows rapid (1-2.5 minutes) administration of lidocaine or a lidocaine-like compound to the lungs, with markedly reduced oropharyngeal deposition. Also, since the PARI eFlow nebulizer is battery powered, it allows the patient more flexibility in treatment location.

The PARI eFlow nebulizer is a single object, multi-use nebulizer designed to be used in the same fashion as other jet nebulizers currently on the market. The difference affecting its function is attributed to its modification replacing compressed air of the jet nebulizer to generate the aerosol from the drug reservoir. The modified PARI eFlow nebulizer instead uses a vibrating, piezoelectric perforated membrane. The use of this vibrating membrane results in a highly efficient nebulizer with enhanced speed and efficiency administration for lidocaine or a lidocaine-like compound with total output rate (TOR) longer than 0.4 g/min and with oropharyngeal deposition typically less than 5%.

The advantage of using an electronic nebulizer that produces an aerosol with the preferred characteristics is that more drug is deposited to the site of action, that is to the central airways, with a lesser residue deposited to the mouth and throat where it would cause numbing and other complications.

PARI eFlow nebulizer, equipped with a vibrating perforated membrane permits adjustment of the particle size distribution and fine tunning to produce substantially all particles with the optimal size and the fast delivery of the drug. The optimal particle size for deposition of the drug substantially into the conducting and central airways is approximately 4.5 microns. Additionally, the eFlow electronic nebulizer modified with vibrating perforated membrane produces primarily the monodisperse aerosol, with a general standard deviation (GSD) in particle size of smaller than 1.7. Such GSD is much smaller than the GSD produced of the particles produced by other nebulizers.

The basic performance specifications for the eFlow nebulizer are presented in Table 5.

TABLE 5

Performance Specifications of eFlow Nebulizer

| eFlow nebulizer | Value |
| --- | --- |
| Mass Median Diameter (MMD) | 3.3-3.8 μm |
| Geometric Standard Deviation (GSD) | approx. 1.6 μm |
| Total Output Rate (TOR) | >0.4 g/min |
| Residual Volume | negligible |

The eFlow is designed to aerosolize all of the aqueous drug placed in the device. A maximum of 150 μl of precipitation may remain on the device walls.

The combination of these benefits results in a treatment time typically of one tenth or less of the current therapies, and as low as 1 minute per 1 mL LSI solution.

In another study, nebulizer Battelle HH5 (Phaser) obtained from Battelle Corporation (now Ventara Corp.), was tested. Results are seen in Table 6. Lidocaine solutions for inhalation containing 14.6% and 17.5% of the drug delivered at a rate of 28.3 L/min (R=585 Ohm$^{-n}$) were nebulized in vitro with the Battelle HH5 (Phaser). Particle sizes as well as deposition on a filter (inhaled dose) were measured upon multiple actuations.

TABLE 6

Nebulizer Performance Tests In Vitro

| | Value |
| --- | --- |
| LSI Phaser with 14.6% Lidocaine | |
| Lidocaine Concentration | 146.5 mg/ml |
| Actuation volume | 16 μl |
| Filter deposition | 2.03 ± 0.08 |
| mg Particles 2.1-9 μm | 89% |
| LSI Phaser with 17.5% Lidocaine | |
| Lidocaine Concentration | 175 mg/ml |
| Actuation volume | 16 μl |
| Filter deposition | 2.46 ± 0.18 mg |
| Particles 2.1-9 μm | 72% |

For lidocaine concentration 17.5% (175 mg/ml, 16 ul per actuation, nominal dose of 2.8 mg), the filter deposition of lidocaine on inhalation filters was between 2.15 and 2.67 mg (mean 2.46±0.18 mg, RSD 7.16%) per actuation. The particle size distribution showed 72% of particles between 2.1 and 9 μm, indicating only partly acceptable nebulization for the purposes of this invention.

For lidocaine or a lidocaine-like compound 14.6% (146.5 mg/ml, 16 ul per actuation, nominal dose of 2.34 mg), the lidocaine deposition on inhalation filters was between 1.86 and 2.13 mg (mean 2.03±0.08 mg, RSD 3.85%) per actuation. A particle size distribution showed 89% of particles between 2.1 and 9 μm. These studies show that, as alternative nebulizer, the Battelle HH5 (Phaser) could be potentially used with the current invention provided that the low drug deposition in the lung could be improved.

Comparative study of the PARI eFlow electronic nebulizer delivering 1 ml, 2 ml and 3 ml doses of lidocaine or a lidocaine-like compound vis-a-vis a time of delivery, is shown in Table 7.

TABLE 7

Drug Delivery by the Modified PARI eFlow Nebulizer

| | Fill Volume | | |
| --- | --- | --- | --- |
| | 1 mL | 2 mL | 3 mL |
| Number of PARI eFlow tested | 1 | 9 | 1 |
| Number of tests | 2 | 18 | 2 |
| Nominal Drug Dose (mg) | 92 | 184 | 276 |
| DD (mg drug on insp. filter ± SD | 48.9 | 98.3 ± 2.6 | 148.8 |
| DD (% drug on insp. filter) ± SD | 53.2% | 53.4 ± 1.4% | 53.9% |
| DDR (mg drug/min) | 22.1 | 22.5 | 24.4 |
| FF (droplets <5.8 μm) measured by LD | 82.0% | 82.0% | 82.0% |
| RD (mg drug) | 40.4 | 81.2 | 122.6 |
| RDDR (mg drug/min) | 18.3 | 18.6 | 20.2 |
| Nebulization time (min) | 2.21 | 4.37 ± 0.60 | 6.09 |

IMP = improved with a vibrating perforated membrane.

In Table 7, the PARI eFlow nebulizer was used to determine the efficacy of the drug delivery. The study was designed to compare nebulization of the nominal drug dose 92 mg in 1, 184 in 2 ml and 276 mg in 3 mL of the solvent. Both delivered dose (DD) and respirable dose (RD) are expressed in mg of drug. Additionally, the drug (mg) delivered per 1 minute (DDR and RDDR) and nebulization were determined. Results seen in the nebulization time column shows that respirable dose 40.4 mg can be delivered in 2.21 minutes, 81.2 mg can be delivered in 4.37 minutes and 122.6 mg of the drug can be delivered by 6 minutes long nebulization.

Results seen in Table 7 clearly show that the use of the PARI eFlow electronic nebulizer results in a significant improvement of the drug delivery rate and that the time of the drug delivery can be substantially shortened while the efficacy of the delivery is not affected by such time shortening.

D. Dry Powder Inhalers

Dry powder is administered as such using devices such as dry powder or meter dose inhalers which deliver the dry powder directly to the lungs.

For use in dry powder inhalers, the lidocaine or a lidocaine-like compound is formulated as a dry powder, as described above, in dosages from 1-100 mg, preferably from 10-50 mg. The particle sizes of the powder are such that when the powder is emitted from the inhaler, it forms an aerosol with a mass median diameter of between about 3.5-10 μm, preferably substantially between 4 μm and about 5 μm.

E. Efficacy of Lidocaine or a Lidocaine-like Compound Nebulization

As described above, the selection and choice of the nebulizer greatly affects efficacy of the delivery of the inhalable lidocaine or a lidocaine-like compound.

A combination of an aerosol formulation of lidocaine or a lidocaine-like compound and a nebulizing device significantly enhances the efficiency and speed of lidocaine or a lidocaine-like compound administration.

Currently, for example the average time for administration of inhaled lidocaine or a lidocaine-like compound solutions using other formulations and nebulizers is 10-20 minutes per dose. Since, at this time, no safe and convenient plastic vial for packaging and storage of the lidocaine solution is available, patients need to use glass vials of i.v. lidocaine, assure that there are no preservatives in the formulation, extract a defined amount of lidocaine from the vial by use of a syringe, and inhale via jet nebulizer. Such inhalation typically requires at least 10-20 minutes.

The time required for the currently available treatments results a significant loss of the drug, loss of the time, places unnecessary burden on the patient and contributes to reduced compliance with the daily regimen.

Furthermore, the nebulizer systems used previously for lidocaine administration are less efficient than new electronic devices. Using these nebulizers, the total deposited dose of drug in the lung is in the 12 to 15% range, at maximum. Approximately 30% of the dispensed drug remains in the nebulizer at the end of treatment, and of the portion that is aerosolized, about 30% is emitted as particles too large or too small to reach the central airways. Oropharyngeal numbing, impairment of the gag reflex, cough, shortness of breath and breathlessness caused by a deposition of the drug in the peripheral and/or upper lungs and other systemic side effects are the consequences of these treatments.

The novel electronic nebulizer, with an output of 8 to 10 microliters/seconds, or 0.48 to 0.60 ml/minute, is capable of delivering drug material 2 to 5 times faster than the prior nebulizers, such as, for example, PARI LC plus jet nebulizer. Furthermore, the novel nebulizer is able to aerosolize more than 90% of the dispensed dose. As a result, administration of a specifically designed formulation of lidocaine or a lidocaine-like compound using the electronic nebulizer leads to substantial improvement in delivery of the drug to the central airways, in a shorter time required for delivery and, depending on the final concentration of lidocaine or a lidocaine-like compound in the inhalable solution, reduces treatment time to as little as one to two minutes.

UTILITY

The method according to this invention is suitable for pre-treatment of lungs prior to inhalation delivery of the primary therapeutically effective agents. The method improves tolerance and deposit of the primary inhalable agent in the targeted area of the lungs. Also, the treatment improves patient's tolerance to smoke, smog, dust and air pollution.

In another use of this invention, aerosolized lidocaine may be used as a prevention in people such as firemen, inner city people, inner city children, smokers, people that get exposed to smoke and steam at the workplace, etc., exposed to smoke, dust, and air pollution.

Medically, the advantages of the current invention are substantially improved safety, efficacy, tolerance, and targeted dosing achieved with the PARI eFlow and other electronic devices.

EXAMPLE 1

Lidocaine or a Lidocaine-like Compound Solution for Inhalation

This example describes the preparation of a solution for inhalation comprising lidocaine or a lidocaine-like compound used for in vivo studies.

Lidocaine solution for inhalation (LSI) is provided as a 1.0 mL sterile, preservative free, nonpyrogenic single dose ampule. The ampules contain 10 or 40 mg of lidocaine hydrochloride, USP (1 mL of 1% or 4% of lidocaine), in a pH range of 5.0 to 7.0. The added sodium chloride content is 6.844 g/L of sodium chloride USP for 1% lidocaine, and 0.351 g/L of sodium chloride USP for 4% lidocaine. The osmolality for both solutions is approximately 275-300 mOsm/kg.

LSI is intended for use in combination with the PARI eFlow nebulizer.

Preparation of the Inhalable Solution Comprising lidocaine-like compounds follows the same preparation protocol.

EXAMPLE 2

Preparation of Dry Powder Comprising Lidocaine or a Lidocaine-like Compound

This example provides methods and procedures used for preparation of lidocaine or a lidocaine-like compound containing inhalable dry powder.

For dry powder formulation of the invention, a purified lidocaine or a lidocaine-like compound is processed to a powder having mass median average diameters ranging from 3 µm to 10 µm by media milling, jet milling, spray drying, or particle precipitation techniques.

Media milling may be accomplished by placing lidocaine or a lidocaine-like compound substance into a mill containing, for example, stainless steel or ceramic balls and rotating or tumbling the material until the desired drug particle size ranges are achieved.

Jet milling uses very high pressure air streams to collide particles with one another, with fine particles of the desired size being recovered from the mill.

Spray drying is achieved by spraying a fine mist of lidocaine or a lidocaine-like compound solution onto a support and drying the particles. The particles are then collected.

Particle precipitation is achieved by adding a co-solvent to spray dried particles. The solubility of the drug falls to the point where solid drug particles are formed. The particles are collected by filtration through 3 µm filter or centrifugation. Precipitation has the advantage of being highly reproducible and can be performed under low temperature conditions, which reduce degradation.

Other technologies available to be used for preparation of dry powders may also be used.

EXAMPLE 3

Dry Powder Inhalers for Use with Lidocaine or a Lidocaine-like Compound Powder

The lidocaine or a lidocaine-like compound dry powder formulations of the invention may be used directly in metered dose or dry powder inhalers.

A metered dose inhaler consists of three components: a canister containing the propellant lidocaine or a lidocaine-like compound suspension, a metering valve designed to deliver accurately metered volumes of the propellant suspension, and an oral adapter which contains a spray orifice from which the metered dose is delivered. In the rest position, the metering chamber of the valve is connected to the drug suspension reservoir via a filling groove or orifice. On depression of the valve this filling groove is sealed and the metering chamber is exposed to atmospheric pressure via the spray orifice in the oral adapter and the valve stem orifice. This rapid pressure reduction leads to flash boiling of the propellant and expulsion of the rapidly expanding mixture from the metering chamber. The liquid/vapor mixture then enters the expansion chamber which is constituted by the internal volume of the valve stem and the oral adapter. The mixture undergoes further expansion before being expelled, under its own pressure, from the spray nozzle. On exit from the spray orifice, the liquid ligaments which are embedded in propellant vapor are torn apart by aerodynamic forces. Typically, at this stage, the droplets are 20 to 30 μm in diameter and are moving at the velocity of sound of the two-phase vapor liquid mixture (approximately 30 meters per second). As the cloud of droplets moves away from the spray nozzle, it entrains air from the surroundings and decelerates, while the propellant evaporates through evaporation, the entrained droplets eventually reach their residual diameter.

At this point, the particles/droplets consist of a powdered lidocaine or a lidocaine-like compound core coated with surfactant. Depending on the concentration and the size of the suspended material the powdered drug core consists of either individual drug particles or aggregates.

An alternated route of lidocaine or a lidocaine-like compound dry powder delivery is by dry powder inhalers.

Excipients commonly used for dry powder formulations are lactose, however in the case of lidocaine or a lidocaine-like compound free base, the addition of the amino acids lysine or leucine will lead to better powder formation.

Effective dosage levels of lidocaine or a lidocaine-like compound for dry powder inhalation and metered dose inhalation result in the application of a nominal dose of at least about 10 mg, and more preferable about 40 mg of lidocaine or a lidocaine-like compound to the conducting and central airways of the patient receiving treatment. Deposited dose are 2 and 20 mg in the conducting and central airways for 10 mg and 40 mg nominal dose, respectively. Depending on the efficiency of the dry powder delivery device, dry powder formulations suitable for use in the invention comprise from about 1.0 to about 50 mg, preferably from about 10 to about 40 mg of powder in an amorphous or crystalline lidocaine or a lidocaine-like compound in particle sizes between 3 μm and 10 μm in mass median average diameter necessary for efficacious delivery of lidocaine or a lidocaine-like compound into the central airways. The dry powder formulation is typically delivered in conjunction with the delivery of the primary drug a and may occur 1 to 4 times daily. The dry powder formulations are temperature stable and have a physiologically acceptable pH of 5.0 to 7.5, preferably 5.5 to 7.0, and long shelf lives.

EXAMPLE 4

Lidocaine Solution for Inhalation used for Treatment of Asthma Patients

This example describes a clinical trial with inhalable lidocaine (10 and 40 mg) for treatment of asthma patients also treated with albuterol.

The clinical trial was performed in a double blinded, placebo controlled study in mild to moderate asthma patients. For the study, 10 mg (1 ml of 1% lidocaine/saline), 40 mg (1 ml of 4% lidocaine/saline) of lidocaine solution for inhalation or placebo (1 ml of saline) was administered by the electronic nebulizer PARI eFlow, modified. The lidocaine solution was administered either alone or in conjunction with administration of albuterol twice daily.

Asthma patients (100 females and 54 males, 31.3±1.8 years of age, $FEV_1$ 78.4±1.8% predicted) were enrolled, randomized to three groups, and treated for 12 weeks. The full individual doses of 1 ml were administered in 2-3 minutes treatment time.

Both doses of lidocaine were found to be well tolerated and safe, and no difference was found in the number of patients with at least one adverse events (AEs) were found between placebo (30/48, 63%), 10 mg lidocaine (39/55, 71%), and 40 mg lidocaine (33/51, 65%). Particularly, there was no difference in the number of patients with one or more respiratory AEs between placebo (14/48, 29%), 10 mg lidocaine or a lidocaine-like compound (16/55, 29%), and 40 mg lidocaine or a lidocaine-like compound (18/51, 35%).

Airway irritation and acute bronchospasm were assessed by measuring spirometry immediately prior to and 30 min post-completion of aerosol administration. A decrease in forced expired volume in one second (FEV1) >20% in the 30 minutes spirometry test was considered evidence of bronchospasm. All patients were tested for bronchospasm upon aerosolization of all three doses mentioned above (LSI 1%, 4%, and placebo), and FEV1 was compared before and after drug application of drug. None of the 154 treated had occurrence of bronchospasm.

The amount of complaints about oropharyngeal numbing was greatly reduced when compared to previous studies with inhaled lidocaine given by other nebulizers. Numbing in all previous studies had been noted in virtually all subjects, whereas the incidence of numbing in this clinical trial was 40% (22/55) and 31.45% (16/51) of treated patients, noted at least once during the course of the 12 week study and 60% in 1% group and 68.6% in 4% group of lidocaine treated patients did not have any complaints of numbing at all.

No loss of gag reflex was reported. No case of tracheal aspiration of food or liquid was reported. Most importantly, there were no reports of bronchospasm upon lidocaine delivery, nor was there any report of a clinically significant $FEV_1$ drop upon lidocaine inhalation (the measure for bronchospasm).

Within the Asthma Quality of Life Questionnaires (AQLQ) (environmental domain), all patients were asked about how they tolerated impact of dust, smoke, and air pollution. When AQLQs were analyzed, a significant improvement was observed at week 12 from the baseline between treatment groups and placebo in the environmental domain of the questions (mean changes were placebo=0.35; 10 mg lidocaine=2.09; and 40 mg lidocaine=2.45; p=0.012 for 10 mg lidocaine v. placebo, p=0.01 for 40 mg v. placebo).

These results indicate a post-treatment improvement of airway susceptibility and asthma in tolerating environmental airway challenges like smoke, dust, pollution, allergens, etc.

The lung deposition of lidocaine is increased two- to three-fold. The same efficacious amount can be delivered in ⅓ of the time used previously. The safety profile is greatly improved, with abolished bronchospasm, greatly reduced incidence of oropharyngeal numbing, loss of gag reflex with lower lung and systemic deposition of lidocaine.

These results confirm that the inhalable lidocaine or a lidocaine-like compound administered according to the invention is safe and tolerable upon its delivery to the conducting airways. None of the descriptions of prior art provided a convenient, tolerable and safe administration of lidocaine or a lidocaine-like compound to the upper and central airways.

What is claimed is:

1. A method for improvement of tolerance for an aerosolized primary therapeutically effective agent delivered to lungs of a patient in need thereof with an inhalable dry powder, comprising steps:

a) preparing an inhalable dry powder consisting essentially of about 10 mg, 40 mg or 100 mg of lidocaine or a lidocaine-like acetanilide and benzamide compound and an excipient selected from the group consisting of lactose, lysine and leucine; wherein said dry powder have a mass median aerodynamic diameter between about 1 μm and about 10 μm with a geometric standard deviation lower than 1.7 b) selecting a dry powder or meter dose inhaler able to generate aerosol of particle sizes between 3.5 and 10 μm;

c) nebulizing said inhalable dry powder into an aerosol having a mass median aerodynamic diameter of particles between about 4 μm and about 5 μm with a geometric standard deviation lower than 1.7; and d) administering said aerosol to said patient immediately before or within 30 minutes before administering said aerosolized primary therapeutically effective agent selected from the group consisting of α-proteinase-inhibitor, amikacin, carbenicillin, ceftazidim, colistin, gentamycin, imipenem, ticarcillin, penicillin, tobramycin, vancomycin, aztreonam, fosfomycin, rifampicin, ciprofloxacin, quinolone, glutathion, pentamidine, nifedipine, verapamil, amiloride, benzamil, furosemide, piretanid, torasemid, heparin, cyclosporine, prednisone, methotrexate, azathoprine, mycophenoline, sirolimus, tacrolimus, mofetil, α-interferone, β-interferone, γ-interferone, interleukin 2, adrenaline, retinoic acid, amphotericin B, beclomethasone, cefoperazone, ciproflaxine, fentanyl, fusafungin, DNA, magnesium sulfate, dextrane, dornase α, hypertonic saline, mannitol. N-acetylcystein, nitroglycerine, nitroprusside sodium, morphine, prostaglandin, indomethacin, budesonide, dexamethasone, aminophylline, ribavirine and human growth factor.

2. The method of claim 1 wherein said lidocaine or a lidocaine-like acetanilide and benzamide compound is selected from the group consisting of tetradecanoic acid [3-(2-diethylamino-acetylamino)-2,4-dimethyl-phenyl]-amide; 2-diethylamino-N-(2,6-dimethyl-3-tridecylamino-phenyl)-acetamide; 2-diethylamino-N-{2,6-dimethyl-3-[5-(4-phenyl-butoxy)-entylaminol]-phenyl}-acetamide; N-(2-diethylamino-ethyl)-4-(4-trifluoromethoxy-benzylamino)-benzamide; N-(2-diethylamino-ethyl)-4-(4-trifluoromethoxy-benzoylamido)-benzamide; N-(2-diethylamino-ethyl)-4-(4-phenyl-benzoylamido)-benzamide; 2-[1,4']bipiperidinyl-1'-yl-N-[2,6-dimethyl-3-(4-phenyl-butylamino)-phenyl]-acetamide; 2-[1,4']bipiperidinyl-1'-yl-N-{2,6-dimethyl-3-[2-(4-trifluoromethoxy-phenyl)-ethylamino]-phenyl}-acetamide; and 2-[1,4']bipiperidinyl-1'-yl-N-(2,6-dimethyl-phenyl)-acetamide and the pharmaceutically acceptable salts thereof.

3. The method of claim 2 wherein said inhalable dry powder is delivered by a dry powder inhaler.

4. The method of claim 2 said inhalable dry powder is delivered by a metered dose inhaler.

5. The method of claim 1 wherein said inhalable dry powder is administered one to four times a day prior to administration of said aerosolized primary therapeutically effective agent or its delivery coincides with a delivery regimen of said aerosolized primary therapeutically effective agent.

6. The method of claim 5 wherein said aerosolized primary therapeutically effective agent is ceftazidim, colistin, gentamycin, imipenem, ticarcillin, tobramycin, vancomycin, aztreonam, fosfomycin, rifampicin, ciprofloxacin, quinolone, glutathion, pentamidine, nifedipine, verapamil, amiloride, benzamil, furosemide, piretanid, torasemid, heparin, cyclosporine, prednisone, methotrexate, azathoprine, mycophenoline, sirolimus, tacrolimus, or mofetil.

7. The method of claim 6 wherein the combination of said inhalable dry powder with said aerosolized primary agent is administered one or two times a day.

8. An inhalable dry powder for delivery to a patient in need thereof, wherein said inhalable dry powder consists essentially of about 10, 40 or about 100 mg of lidocaine or a lidocaine-like acetanilide and benzamide compound, an excipient selected from the group consisting of lactose, lysine, and leucine, and in combination with an aerosolable primary therapeutically effective agent selected from the group consisting of α-proteinase-inhibitor, amikacin, carbenicillin, ceftazidim, colistin, gentamycin, imipenem, ticarcillin, penicillin, tobramycin, vancomycin, aztreonam, fosfomycin, rifampicin, ciprofloxacin, quinolone, glutathion, pentamidine, nifedipine, verapamil, amiloride, benzamil, furosemide, piretanid, torasemid, heparin, cyclosporine, prednisone, methotrexate, azathoprine, mycophenoline, sirolimus, tacrolimus, mofetil, α-interferone, β-interferone, γ-interferone, interleukin 2, adrenaline, retinoic acid, amphotericin B, beclomethasone, cefoperazone, ciproflaxine, fentanyl, fusafungin, DNA, magnesium sulfate, dextrane, dornase α, hypertonic saline, mannitol. N-acetylcystein, nitroglycerine, nitroprusside sodium, morphine, prostaglandin, indomethacin, budesonide, dexamethasone, aminophylline, ribavirine and human growth factor.

9. The composition of claim 8 wherein said inhalable dry powder has a particle size with a mass median aerodynamic diameter from about 1 μm to about 5 μm.

10. The composition of claim 8 wherein said lidocaine or lidocaine-like acetanilide and benzamide compound is selected from the group consisting of tetradecanoic acid [3-(2-diethylamino-acetylamino)-2,4-dimethyl-phenyl]-amide; 2-diethylamino-N-(2,6-dimethyl-3-tridecylamino-phenyl)-acetamide; 2-diethylamino-N-{2,6-dimethyl-3-[5-(4-phenyl-butoxy)-entylamino]-phenyl}-acetamide; N-(2-diethylamino-ethyl)-4-(4-trifluoromethoxy-benzylamino)-benzamide; N-(2-diethylamino-ethyl)-4-(4-trifluoromethoxy-benzoylamido)-benzamide; N-(2-diethylamino-ethyl)-4-(4-phenyl-benzoylamido)-benzamide; 2-[1,4']bipiperidinyl-1'-yl-N-[2,6-dimethyl-3-(4-phenyl-butylamino)-phenyl]-acetamide; 2-[1,4']bipiperidinyl-1'-yl-N-{2,6-dimethyl-3-[2-(4-trifluoromethoxy-phenyl)-ethylaminol]-phenyl}-acetamide; and 2-[1,4']bipiperidinyl-1'-yl-N-(2,6-dimethyl-phenyl)-acetamide and the pharmaceutically acceptable salts thereof.

11. The composition of claim 10 wherein said dry powder is milled, spray dried, lyophilized or particle precipitated.

12. The composition of claim 9 wherein said patient is a lung transplant patient.

13. The composition of claim 9 wherein said patient is an organ transplant patient.

14. The composition of claim 13 wherein said organ transplant is heart transplant, kidney transplant, liver transplant or spleen transplant.

15. A method for improvement of tolerance and deposition of an aerosolized immunosuppressive drug used for treatment of an organ transplant patient with an inhalable dry powder, said method comprising steps:

a) preparing said inhalable dry powder consisting essentially of about 10 mg, 40 mg or 100 mg of lidocaine or a lidocaine-like acetanilide and benzamide compound and an excipient selected from the group consisting of lactose, lysine and leucine; wherein said inhalable dry powder has a mass medium aerodynamic diameter of particles between about 0.1 μm and about 10 μm with a geometric standard deviation lower than 1.7;

b) selecting a dry powder or meter dose inhaler able to generate aerosol of particle sizes between 3.5 and 10 μm;

c) nebulizing said dry powder into an aerosol having a mass median aerodynamic diameter of particles between about 4 μm and about 5 μm with a geometric standard deviation lower than 1.7; and d) administering said aerosol to said patient immediately before or within 30 minutes before administering the aerosolized immunosuppressive drug.

16. The method of claim 15 wherein said dry powder consisting essentially of about 10 mg of lidocaine or a lidocaine-like acetanilide and benzamide compound and an excipient selected from the group consisting of lactose, lysine, and leucine, and wherein said immunosuppressive drug is cyclosporine.

17. The method of claim 16 wherein the inhaler is the dry powder inhaler.

18. The method of claim 16 wherein the inhaler is metered-dose inhaler.

19. The method of claim 18 wherein said dry powder is administered within 30 minutes before administration of the immunosuppressive drug.

20. The method of claim 18 wherein said dry powder is administered concurrently with administration of the immunosuppressive drug.

21. A method for improvement of tolerance for smoke, smog, air pollution, dust or allergens in a human subject in need thereof, said method comprising steps:

a) preparing an inhalable dry powder comprising about 10 mg, 40 mg or 100 mg of lidocaine or a lidocaine-like acetanilide and benzamide compound and an excipient selected from the group consisting of lactose, lysine and leucine, wherein said lidocaine-like compound is selected from the group consisting of tetradecanoic acid [3-(2-diethylamino-acetylamino)-2,4-dimethyl-phenyl]-amide; 2-diethylamino-N-(2,6-dimethyl-3-tridecylamino-phenyl)-acetamide; 2-diethylamino-N-{2,6-dimethyl-3-[5-(4-phenyl-butoxy)-entylaminol]-phenyl}-acetamide; N-(2-diethylamino-ethyl)-4-(4-trifluoromethoxy-benzylamino)-benzamide; N-(2-diethylamino-ethyl)-4-(4-trifluoromethoxy-benzoylamido)-benzamide; N-(2-diethylamino-ethyl)-4-(4-phenyl-benzoylamido)-benzamide; 2-[1,4'] bipiperidinyl-1'-yl-N-[2,6-dimethyl-3-(4-phenyl-butylamino)-phenyl]-acetamide; 2-[1,4']bipiperidinyl-1'-yl-N-{2,6-dimethyl-3-[2-(4-trifluoromethoxy-phenyl)-ethylamino]-phenyl}-acetamide; and 2-[1,4'] bipiperidinyl-1'-yl-N-(2,6-dimethyl-phenyl)-acetamide and the pharmaceutically acceptable salts thereof;

b) selecting a dry powder inhaler or meter dose inhaler able to generate aerosol of particle sizes between 3.5 and 10 μm;

c) nebulizing said dry powder into an aerosol having a mass median aerodynamic diameter of particles between about 4 μm and about 5 μm with a geometric standard deviation lower than 1.7; and d) administering said aerosol to said a human subject exposed to or following exposure to smoke, smog, air pollution, dust or allergens, immediately before or immediately after the exposure.

* * * * *